United States Patent
Roe et al.

(10) Patent No.: US 9,216,116 B2
(45) Date of Patent: Dec. 22, 2015

(54) ABSORBENT ARTICLES WITH CHANNELS

(71) Applicant: The Procter & Gamble Company, Cincinnati, OH (US)

(72) Inventors: Donald Carroll Roe, West Chester, OH (US); Carsten Heinrich Kreuzer, Schwalbach am Taunus (DE); Rodrigo Rosati, Schwalbach am Taunus (DE); Maja Wciorka, Schwalbach am Taunus (DE)

(73) Assignee: The Procter & Gamble Company, Cincinnati, OH (US)

( * ) Notice: Subject to any disclaimer, the term of this patent is extended or adjusted under 35 U.S.C. 154(b) by 238 days.

(21) Appl. No.: 13/709,254

(22) Filed: Dec. 10, 2012

(65) Prior Publication Data

US 2014/0163511 A1 Jun. 12, 2014

(51) Int. Cl.
| | | |
|---|---|---|
| *A61F 13/15* | (2006.01) | |
| *A61F 13/20* | (2006.01) | |
| *A61F 13/49* | (2006.01) | |
| *A61F 13/475* | (2006.01) | |
| *A61F 13/532* | (2006.01) | |

(Continued)

(52) U.S. Cl.
CPC ....... *A61F 13/49007* (2013.01); *A61F 13/4704* (2013.01); *A61F 13/4756* (2013.01); *A61F 13/49001* (2013.01); *A61F 13/532* (2013.01); *A61F 13/533* (2013.01); *A61F 13/535* (2013.01); *A61F 13/536* (2013.01)

(58) Field of Classification Search
CPC ............ A61F 13/49001; A61F 13/495; A61F 13/511; A61F 13/514; A61F 13/532; A61F 13/535; A61F 13/537
See application file for complete search history.

(56) References Cited

U.S. PATENT DOCUMENTS 1,733,997 A  10/1929  Marr
1,734,499 A  11/1929  Marinsky
(Continued)

FOREIGN PATENT DOCUMENTS

CA  2001370  4/1990
CA  2291997  6/2000
(Continued)

OTHER PUBLICATIONS

All Office Actions, Responses, and Claims, U.S. Appl. No. 13/709,169.
(Continued)

*Primary Examiner* — Jason Flick
*Assistant Examiner* — Aundria Hairell
(74) *Attorney, Agent, or Firm* — Christian M. Best

(57) ABSTRACT

The present disclosure is directed, in part, to an absorbent article comprising an absorbent core disposed at least partially intermediate the topsheet and the backsheet and comprising a core wrap enclosing an absorbent material. The core wrap comprises a first material and a second material. The first material forms a C-wrap at least partially around the second material. The absorbent material comprises at least 80% of superabsorbent polymers by weight of the absorbent material. The absorbent core comprises a channel substantially free of the superabsorbent polymers and at least partially oriented in a longitudinal direction of the article. The channel has an arcuate portion facing a longitudinal axis of the article. An angle between a tangent line of the arcuate portion and the longitudinal axis is greater than or equal to 20 degrees.

26 Claims, 20 Drawing Sheets

(51) Int. Cl.
    *A61F 13/533*    (2006.01)
    *A61F 13/535*    (2006.01)
    *A61F 13/536*    (2006.01)
    *A61F 13/47*     (2006.01)

(56) References Cited

U.S. PATENT DOCUMENTS

| | | |
|---|---|---|
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,003 A | 4/1957 | Norden |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,071,138 A | 1/1963 | Gustavo |
| 3,180,335 A | 4/1965 | Duncan et al. |
| 3,207,158 A | 9/1965 | Yoshitake et al. |
| 3,227,160 A | 1/1966 | Joy |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr et al. |
| 4,469,710 A | 9/1984 | Rielley et al. |
| 4,475,912 A | 10/1984 | Coates |
| 4,490,148 A | 12/1984 | Beckeström |
| 4,507,438 A | 3/1985 | Obayashi et al. |
| 4,515,595 A | 5/1985 | Kievit et al. |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola et al. |
| 4,578,072 A | 3/1986 | Lancaster |
| 4,578,702 A | 3/1986 | Campbell |
| 4,585,448 A | 4/1986 | Enloe |
| 4,585,450 A | 4/1986 | Rosch et al. |
| 4,589,878 A | 5/1986 | Mitrani |
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman et al. |
| 4,623,342 A | 11/1986 | Ito et al. |
| 4,624,666 A | 11/1986 | Derossett |
| 4,629,643 A | 12/1986 | Curro et al. |
| 4,636,207 A | 1/1987 | Buell |
| 4,641,381 A | 2/1987 | Heran et al. |
| 4,646,510 A | 3/1987 | McIntyre |
| 4,662,875 A | 5/1987 | Hirotsu et al. |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant et al. |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert et al. |
| 4,747,846 A | 5/1988 | Boland et al. |
| 4,753,648 A | 6/1988 | Jackson |
| 4,773,905 A | 9/1988 | Molee et al. |
| 4,784,892 A | 11/1988 | Storey et al. |
| 4,785,996 A | 11/1988 | Ziecker et al. |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Fröidh et al. |
| 4,806,598 A | 2/1989 | Morman |
| 4,808,176 A | 2/1989 | Kielpikowski |
| 4,808,178 A | 2/1989 | Aziz |

(56) References Cited

U.S. PATENT DOCUMENTS

| | | |
|---|---|---|
| 4,826,880 A | 5/1989 | Lesniak et al. |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki et al. |
| 4,892,535 A | 1/1990 | Bjornberg |
| 4,892,536 A | 1/1990 | DesMarais et al. |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,936,839 A | 6/1990 | Molee et al. |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Roe et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | Desmarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | LaVon et al. |
| 5,366,782 A | 11/1994 | Curro et al. |
| 5,382,610 A | 1/1995 | Harada et al. |
| 5,387,207 A | 2/1995 | Dyer et al. |
| 5,387,208 A | 2/1995 | Ashton et al. |
| 5,387,209 A | 2/1995 | Yamamoto et al. |
| 5,389,095 A | 2/1995 | Suzuki |
| 5,397,316 A | 3/1995 | LaVon et al. |
| 5,397,317 A | 3/1995 | Thomas |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,429,630 A | 7/1995 | Beal et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Hines et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,559,335 A | 9/1996 | Zing et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,586,979 A | 12/1996 | Thomas |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | DiPalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |

(56) References Cited

U.S. PATENT DOCUMENTS

| | | |
|---|---|---|
| 5,624,423 A | 4/1997 | Anjur |
| 5,624,424 A | 4/1997 | Saisaka et al. |
| 5,625,222 A | 4/1997 | Yoneda et al. |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe et al. |
| 5,635,271 A | 6/1997 | Zafiroglu |
| 5,637,106 A | 6/1997 | Mitchell |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman et al. |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | McDowall et al. |
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,925,439 A | 7/1999 | Haubach |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | Van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,290,686 B1 | 9/2001 | Tanzer et al. |
| 6,306,122 B1 | 10/2001 | Narawa et al. |
| 6,315,765 B1 | 11/2001 | Datta |
| 6,319,239 B1 | 11/2001 | Daniels et al. |
| 6,322,552 B1 | 11/2001 | Blenke et al. |
| 6,325,787 B1 | 12/2001 | Roe et al. |
| 6,326,525 B1 | 12/2001 | Hamajima |
| 6,330,735 B1 | 12/2001 | Hahn et al. |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |

(56) References Cited

U.S. PATENT DOCUMENTS

| | | | |
|---|---|---|---|
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,342 B2 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Graef |
| 6,524,294 B1 | 2/2003 | Hilston et al. |
| 6,525,240 B1 | 2/2003 | Graef |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Gillies et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B1 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,129 B2 | 3/2004 | Ando et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,204 B1 | 4/2004 | Roe et al. |
| 6,716,205 B2 | 4/2004 | Popp et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef |
| 6,790,798 B1 | 9/2004 | Suzuki et al. |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Popp |
| 6,858,771 B2 | 2/2005 | Yoshimasa |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Henry et al. |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 6,982,052 B2 | 1/2006 | Daniels et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kuroda et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |

(56) References Cited

U.S. PATENT DOCUMENTS

| | | |
|---|---|---|
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,163,528 B2 | 1/2007 | Christon et al. |
| 7,166,190 B2 | 1/2007 | Graef |
| 7,169,136 B2 | 1/2007 | Otsubo |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,241,280 B2 | 7/2007 | Christen et al. |
| 7,250,481 B2 | 7/2007 | Jaworek et al. |
| 7,252,657 B2 | 8/2007 | Mishima |
| 7,265,258 B2 | 9/2007 | Hamilton |
| 7,270,651 B2 | 9/2007 | Adams et al. |
| 7,285,178 B2 | 10/2007 | Mischler et al. |
| RE39,919 E | 11/2007 | Dodge, II et al. |
| 7,306,582 B2 | 12/2007 | Adams et al. |
| 7,311,696 B2 | 12/2007 | Christen et al. |
| 7,311,968 B2 | 12/2007 | Ehrnsperger et al. |
| 7,312,372 B2 | 12/2007 | Miyama |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima |
| 7,504,552 B2 | 3/2009 | Tamura |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi |
| 7,550,646 B2 | 6/2009 | Tamura |
| 7,563,257 B2 | 7/2009 | Nakajima |
| 7,588,561 B2 | 9/2009 | Kenmochi |
| 7,594,904 B2 | 9/2009 | Rosenfeld |
| 7,598,428 B2 | 10/2009 | Gustavsson et al. |
| 7,625,363 B2 | 12/2009 | Yoshimasa |
| 7,641,642 B2 | 1/2010 | Murai et al. |
| 7,648,490 B2 | 1/2010 | Kuroda |
| 7,652,111 B2 | 1/2010 | Hermeling et al. |
| 7,666,173 B2 | 2/2010 | Mishima |
| 7,666,174 B2 | 2/2010 | Kawakami et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld |
| 7,696,402 B2 | 4/2010 | Nishikawa |
| 7,708,725 B2 | 5/2010 | Tamagawa |
| 7,717,150 B2 | 5/2010 | Manabe |
| 7,722,587 B2 | 5/2010 | Suzuki et al. |
| 7,722,590 B2 | 5/2010 | Tsuji |
| 7,727,217 B2 | 6/2010 | Hancock-Cooke |
| 7,736,351 B2 | 6/2010 | Nigam |
| 7,737,324 B2 | 6/2010 | LaVon et al. |
| 7,744,576 B2 | 6/2010 | Busam et al. |
| 7,744,578 B2 | 6/2010 | Tanio et al. |
| 7,750,203 B2 | 7/2010 | Busam et al. |
| 7,754,822 B2 | 7/2010 | Daniel et al. |
| 7,754,940 B2 | 7/2010 | Brisebois |
| 7,759,540 B2 | 7/2010 | Litvay et al. |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao |
| 7,857,797 B2 | 12/2010 | Kudo |
| 7,858,842 B2 | 12/2010 | Komatsu |
| 7,884,259 B2 | 2/2011 | Hanao |
| 7,888,549 B2 | 2/2011 | Jansson |
| 7,910,797 B2 | 3/2011 | Nandrea |
| 7,931,636 B2 | 4/2011 | LaVon et al. |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur |
| 7,951,126 B2 | 5/2011 | Nanjyo |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,239 B2 | 5/2012 | LaVon et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama |
| 8,246,594 B2 | 8/2012 | Sperl et al. |
| 8,258,367 B2 | 9/2012 | Lawson et al. |
| 8,268,424 B1 | 9/2012 | Suzuki |
| 8,273,943 B2 | 9/2012 | Noda |
| 8,283,516 B2 | 10/2012 | Litvay |
| 8,317,766 B2 | 11/2012 | Naoto |
| 8,317,768 B2 | 11/2012 | Larsson |
| 8,319,005 B2 | 11/2012 | Becker et al. |
| 8,343,123 B2 | 1/2013 | Noda |
| 8,343,296 B2 | 1/2013 | Blessing et al. |
| 8,360,977 B2 | 1/2013 | Marttila |
| 8,361,047 B2 | 1/2013 | Mukai |
| 8,377,025 B2 | 2/2013 | Nakajima |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | LaVon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani |
| 2001/0037101 A1 | 11/2001 | Allan et al. |
| 2001/0044610 A1 | 11/2001 | Kim |
| 2002/0007167 A1 | 1/2002 | Dan |
| 2002/0007169 A1 | 1/2002 | Graef et al. |
| 2002/0016122 A1 | 2/2002 | Curro et al. |

(56) References Cited

U.S. PATENT DOCUMENTS

| | | |
|---|---|---|
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi |
| 2002/0072471 A1 | 6/2002 | Ikeuchi et al. |
| 2002/0082575 A1 | 6/2002 | Dan |
| 2002/0087139 A1 | 7/2002 | Popp et al. |
| 2002/0095127 A1 | 7/2002 | Fish et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0109839 A1 | 6/2003 | Costea et al. |
| 2003/0114811 A1 | 6/2003 | Christon et al. |
| 2003/0114816 A1 | 6/2003 | Underhill |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0158531 A1 | 8/2003 | Chmielewski |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127131 A1 | 7/2004 | Potnis |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |
| 2004/0170813 A1 | 9/2004 | Digiacomantonio et al. |
| 2004/0193127 A1 | 9/2004 | Hansson |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef |
| 2005/0101929 A1 | 5/2005 | Waksmundzki et al. |
| 2005/0137543 A1 | 6/2005 | Underhill et al. |
| 2005/0148258 A1 | 7/2005 | Chakravarty |
| 2005/0148990 A1 | 7/2005 | Shimoe |
| 2005/0154363 A1 | 7/2005 | Minato |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069367 A1 | 3/2006 | Waksmundzki et al. |
| 2006/0069371 A1 | 3/2006 | Ohashi et al. |
| 2006/0073969 A1 | 4/2006 | Torii et al. |
| 2006/0081348 A1 | 4/2006 | Graef |
| 2006/0129114 A1 | 6/2006 | Mason et al. |
| 2006/0142724 A1 | 6/2006 | Watanabe |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | Lavon et al. |
| 2006/0271010 A1 | 11/2006 | LaVon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0049892 A1 | 3/2007 | Lord et al. |
| 2007/0049897 A1 | 3/2007 | LaVon et al. |
| 2007/0073253 A1 | 3/2007 | Miyama |
| 2007/0078422 A1 | 4/2007 | Glaug |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun |
| 2007/0244455 A1 | 10/2007 | Hansson et al. |
| 2007/0246147 A1 | 10/2007 | Venturino et al. |
| 2007/0282288 A1 | 12/2007 | Noda |
| 2007/0282290 A1 | 12/2007 | Cole |

(56) References Cited

U.S. PATENT DOCUMENTS

| | | |
|---|---|---|
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda |
| 2008/0125735 A1 | 5/2008 | Busam et al. |
| 2008/0132864 A1 | 6/2008 | Lawson et al. |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto |
| 2008/0268194 A1 | 10/2008 | Kim et al. |
| 2008/0274227 A1 | 11/2008 | Boatman et al. |
| 2008/0281287 A1 | 11/2008 | Marcelo |
| 2008/0294140 A1 | 11/2008 | Ecker et al. |
| 2008/0312617 A1 | 12/2008 | Hundorf et al. |
| 2008/0312618 A1 | 12/2008 | Hundorf et al. |
| 2008/0312619 A1 | 12/2008 | Hundorf et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah |
| 2009/0112175 A1 | 4/2009 | Bissah et al. |
| 2009/0157022 A1 | 6/2009 | Macdonald |
| 2009/0192035 A1 | 7/2009 | Stueven et al. |
| 2009/0240220 A1 | 9/2009 | Macdonald |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo |
| 2009/0318884 A1 | 12/2009 | Meyer et al. |
| 2010/0051166 A1 | 3/2010 | Hundorf et al. |
| 2010/0062165 A1 | 3/2010 | Suzuki |
| 2010/0062934 A1 | 3/2010 | Suzuki |
| 2010/0063470 A1 | 3/2010 | Suzuki |
| 2010/0068520 A1 | 3/2010 | Stueven et al. |
| 2010/0100065 A1 | 4/2010 | Bianco |
| 2010/0115237 A1 | 5/2010 | Brewer et al. |
| 2010/0121296 A1 | 5/2010 | Noda |
| 2010/0137773 A1 | 6/2010 | Gross |
| 2010/0137823 A1 | 6/2010 | Corneliusson |
| 2010/0198179 A1 | 8/2010 | Noda |
| 2010/0228210 A1 | 9/2010 | Busam et al. |
| 2010/0241096 A1 | 9/2010 | LaVon et al. |
| 2010/0241097 A1 | 9/2010 | Nigam et al. |
| 2010/0262099 A1 | 10/2010 | Klofta |
| 2010/0274208 A1 | 10/2010 | Gabrielii |
| 2010/0274210 A1 | 10/2010 | Noda |
| 2010/0312208 A1 | 12/2010 | Bond et al. |
| 2010/0324521 A1 | 12/2010 | Mukai |
| 2010/0324523 A1 | 12/2010 | Mukai |
| 2011/0041999 A1 | 2/2011 | Hundorf et al. |
| 2011/0060303 A1 | 3/2011 | Bissah |
| 2011/0066127 A1 | 3/2011 | Kuwano |
| 2011/0071486 A1 | 3/2011 | Harada |
| 2011/0092944 A1 | 4/2011 | Sagisaka |
| 2011/0112498 A1 | 5/2011 | Nhan et al. |
| 2011/0125120 A1 | 5/2011 | Nishitani |
| 2011/0130732 A1 | 6/2011 | Jackels et al. |
| 2011/0130737 A1 | 6/2011 | Sagisaka |
| 2011/0137276 A1 | 6/2011 | Yoshikawa |
| 2011/0144602 A1 | 6/2011 | Long |
| 2011/0144604 A1 | 6/2011 | Noda |
| 2011/0144606 A1 | 6/2011 | Nandrea |
| 2011/0152813 A1 | 6/2011 | Ellingson |
| 2011/0166540 A1 | 7/2011 | Yang et al. |
| 2011/0172630 A1 | 7/2011 | Nomoto |
| 2011/0174430 A1 | 7/2011 | Zhao |
| 2011/0208147 A1 | 8/2011 | Kawakami et al. |
| 2011/0250413 A1 | 10/2011 | Lu et al. |
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda |
| 2011/0295222 A1 | 12/2011 | Becker et al. |
| 2011/0319846 A1 | 12/2011 | Rinnert et al. |
| 2011/0319848 A1 | 12/2011 | McKiernan et al. |
| 2011/0319851 A1 | 12/2011 | Kudo |
| 2012/0004633 A1 | 1/2012 | Marcelo |
| 2012/0016326 A1 | 1/2012 | Brennan et al. |
| 2012/0022479 A1 | 1/2012 | Cotton |
| 2012/0035566 A1 | 2/2012 | Sagisaka |
| 2012/0035576 A1 | 2/2012 | Ichikawa |
| 2012/0064792 A1 | 3/2012 | Bauduin |
| 2012/0071848 A1 | 3/2012 | Zhang |
| 2012/0165771 A1 | 6/2012 | Ruman et al. |
| 2012/0165776 A1 | 6/2012 | McGregor et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku |
| 2012/0253306 A1 | 10/2012 | Otsubo |
| 2012/0256750 A1 | 10/2012 | Novak |
| 2012/0271262 A1 | 10/2012 | Venturino |
| 2012/0170779 A1 | 12/2012 | Rosati et al. |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah |
| 2012/0323202 A1 | 12/2012 | Bissah |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van De Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0171893 A1 | 6/2014 | Lawson et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2015/0065986 A1 | 3/2015 | Blessing et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 1371671 | 2/2001 |
| CN | 2527254 Y | 12/2002 |
| CN | 2535020 Y | 2/2003 |

(56) References Cited

FOREIGN PATENT DOCUMENTS

| | | |
|---|---|---|
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 149880 | 7/1985 |
| EP | 0149880 A2 | 7/1985 |
| EP | 203289 | 12/1986 |
| EP | 0203289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 0394274 | 7/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 0737055 | 8/1998 |
| EP | 863733 | 9/1998 |
| EP | 971751 | 9/1998 |
| EP | 0875224 | 11/1998 |
| EP | 875224 A1 | 11/1998 |
| EP | 880955 | 12/1998 |
| EP | 891758 | 1/1999 |
| EP | 0893115 | 1/1999 |
| EP | 0724418 | 3/1999 |
| EP | 0725613 | 3/1999 |
| EP | 0725616 | 3/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 0778762 | 4/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 0796068 | 5/2001 |
| EP | 1116479 A2 | 7/2001 |
| EP | 0790839 | 8/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 1263374 B1 | 12/2002 |
| EP | 0737056 | 1/2003 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1621166 | 2/2006 |
| EP | 1621167 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |

(56) References Cited

FOREIGN PATENT DOCUMENTS

| | | |
|---|---|---|
| EP | 2055279 A1 | 5/2009 |
| EP | 2093049 | 8/2009 |
| EP | 2130522 | 12/2009 |
| EP | 1621165 | 4/2010 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2583377 | 12/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/KOL/1999 | 10/2005 |
| IN | 212479 B | 3/2007 |
| IN | 208543 B | 8/2007 |
| IN | 0980/MUM/2009 | 6/2009 |
| JP | 5572928 U | 5/1980 |
| JP | 598322 U | 1/1984 |
| JP | 630148323 U | 9/1988 |
| JP | 2107250 | 4/1990 |
| JP | 03224481 B2 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | 10328232 | 12/1998 |
| JP | 11033056 A | 2/1999 |
| JP | 11318980 | 11/1999 |
| JP | 11320742 | 11/1999 |
| JP | 2000232985 | 8/2000 |
| JP | 2000238161 | 9/2000 |
| JP | 2001037810 | 2/2001 |
| JP | 2001046435 A | 2/2001 |
| JP | 2001120597 | 5/2001 |
| JP | 2001158074 | 6/2001 |
| JP | 2001178768 A | 7/2001 |
| JP | 2001198157 | 7/2001 |
| JP | 2001224626 A | 8/2001 |
| JP | 2001277394 | 10/2001 |
| JP | 03420481 B2 | 11/2001 |
| JP | 2001321397 | 11/2001 |
| JP | 2001353174 A | 12/2001 |
| JP | 2002052042 A | 2/2002 |
| JP | 2002065718 | 3/2002 |
| JP | 2002113800 A | 4/2002 |
| JP | 2002165832 | 6/2002 |
| JP | 2002165836 | 6/2002 |
| JP | 2002178429 | 6/2002 |
| JP | 2002272769 A | 9/2002 |
| JP | 2002320641 | 11/2002 |
| JP | 2002325792 A | 11/2002 |
| JP | 2002325799 A | 11/2002 |
| JP | 2002369841 A | 12/2002 |
| JP | 2003126140 | 5/2003 |
| JP | 2003153955 A | 5/2003 |
| JP | 2003265523 | 9/2003 |
| JP | 2003265524 A | 9/2003 |
| JP | 2003275237 | 9/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006110329 | 4/2006 |
| JP | 2006513824 | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |

(56) References Cited

FOREIGN PATENT DOCUMENTS

| | | |
|---|---|---|
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 A | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 | 9/2012 |
| JP | 05089269 B2 | 9/2012 |
| JP | 05113146 B2 | 10/2012 |
| JP | 05129536 B2 | 11/2012 |
| JP | 05105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9219198 | 11/1992 |
| WO | WO9321237 | 10/1993 |
| WO | WO9321879 | 11/1993 |
| WO | WO9510996 | 4/1995 |
| WO | WO9511652 | 5/1995 |
| WO | WO9514453 | 6/1995 |
| WO | WO9515139 | 6/1995 |
| WO | WO9516424 | 6/1995 |
| WO | WO9516746 | 6/1995 |
| WO | WO9519753 | 7/1995 |
| WO | WO9521596 | 8/1995 |
| WO | WO9524173 | 9/1995 |
| WO | WO9526209 | 10/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO9629967 | 10/1996 |
| WO | WO9711659 | 4/1997 |
| WO | WO9717922 | 5/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO0000235 | 1/2000 |
| WO | WO0032145 | 6/2000 |
| WO | WO0059430 | 10/2000 |
| WO | WO0115647 | 3/2001 |
| WO | WO0126596 | 4/2001 |
| WO | WO0207663 | 1/2002 |
| WO | WO0232962 | 4/2002 |
| WO | WO02064877 | 8/2002 |
| WO | WO02067809 | 9/2002 |
| WO | WO03009794 | 2/2003 |
| WO | WO03039402 | 5/2003 |
| WO | WO03053297 | 7/2003 |
| WO | WO03079946 | 10/2003 |
| WO | WO03101622 | 12/2003 |
| WO | WO03105738 | 12/2003 |
| WO | WO2004021946 | 3/2004 |
| WO | WO2004049995 | 6/2004 |
| WO | WO2004071539 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2006104024 | 5/2006 |
| WO | WO2006059922 | 6/2006 |
| WO | WO2006062258 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007142145 | 12/2007 |

(56) References Cited

FOREIGN PATENT DOCUMENTS

| | | |
|---|---|---|
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO2011053044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO2012090508 | 7/2012 |
| WO | WO2012091016 | 7/2012 |
| WO | WO2012101934 | 8/2012 |
| WO | WO2012102034 | 8/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013060733 | 5/2013 |
| WO | WO2014078247 | 5/2014 |

OTHER PUBLICATIONS

All Office Actions, Responses and Claims, U.S. Appl. No. 13/709,254.
International Search Report and Written Opinion, PCT/2013/073353, date of mailing Mar. 4, 2014.
All Office Actions, Responses, and Claims, U.S. Appl. No. 13/709,169, Sep. 2015.
All Office Actions, Responses and Claims, U.S. Appl. No. 13/709,244, Sep. 2015.

… (US 9,216,116 B2)

ABSORBENT ARTICLES WITH CHANNELS

FIELD

The present disclosure is generally directed to absorbent articles for personal hygiene such as baby diapers, training pants, adult incontinence products, and/or sanitary napkins. The absorbent articles may each comprise channels and/or pockets.

BACKGROUND

Absorbent articles for personal hygiene, such as disposable diapers for infants, training pants for toddlers, adult incontinence undergarments, and/or sanitary napkins are designed to absorb and contain body exudates, in particular large quantities of urine or menses. These absorbent articles comprise several layers providing different functions, for example, a topsheet, a backsheet, and an absorbent core disposed between the topsheet and the backsheet, among other layers.

The function of the absorbent core is to absorb and retain the exudates for a prolonged amount of time, for example, overnight for a diaper, minimize re-wet to keep the wearer dry, and avoid soiling of clothes or bed sheets. The majority of currently marketed absorbent articles comprise as absorbent material which is a blend of comminuted wood pulp with superabsorbent polymers (SAP) in particulate form, also called absorbent gelling materials (AGM). Absorbent articles having a core consisting essentially of SAP as absorbent material (so called "airfelt-free" cores) have also been proposed but are less common than traditional mixed cores.

Some absorbent articles may typically comprise leg cuffs which provide improved containment of liquids and other body exudates. Leg cuffs may also be referred to as leg bands, side flaps, barrier cuffs, or elastic cuffs. Usually, each leg cuff comprises one or more elastic strings or elements comprised in the chassis of the diaper, for example, between the topsheet and backsheet in the area of the leg openings to provide an effective seal while the absorbent article is in use. These elasticized elements which are substantially planar with the chassis of the absorbent article will be referred to herein as gasketing cuffs. It is also usual for the leg cuffs to comprise raised elasticized flaps, herein referred to as barrier leg cuffs, which improve the containment of fluid in the leg-torso joint regions.

Absorbent articles generally have a high absorbent capacity and the absorbent core may expand several times its weight and volume. These increases may cause the absorbent articles to sag in the crotch region as they become saturated with liquid, which may cause the barrier leg cuffs to partially lose contact with the wearer's skin. This may lead to a loss of functionality of the barrier leg cuffs, with the increased possibly of leakage.

Although various solutions to this problem have been proposed, the field can benefit from additional channel and/or pocket configurations that improved leakage prevention in absorbent articles.

SUMMARY

In an embodiment, the present disclosure is directed, in part, to an absorbent article that may comprise a front waist edge or front edge, a rear waist edge or rear edge longitudinally opposing the front waist edge, and a longitudinal axis extending from a midpoint of the front waist edge to a midpoint of the rear waist edge. The absorbent article may comprise a liquid permeable topsheet, a liquid impermeable backsheet, and a pair of barrier leg cuffs extending at least partially between the front waist edge and the rear waist edge on opposite sides of the longitudinal axis. Each barrier leg cuff may comprise a proximal edge joined to the topsheet or the backsheet and a free terminal edge. The absorbent article may comprise an absorbent core disposed at least partially intermediate the topsheet and the backsheet and may comprise a core wrap enclosing an absorbent material. The core wrap may comprise a first material and a second material. The first material may form a C-wrap at least partially around the second material. The absorbent material may comprise at least 80% of superabsorbent polymers by weight of the absorbent material. The absorbent core may comprise a channel substantially free of the superabsorbent polymers and at least partially oriented in the longitudinal direction of the article. The channel may have an arcuate portion facing the longitudinal axis. An angle between a tangent line of the arcuate portion and the longitudinal axis may be greater than or equal to 20 degrees. Other embodiments are also within the scope of the present disclosure, including embodiments for sanitary napkins.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

DETAILED DESCRIPTION

Figure 1:
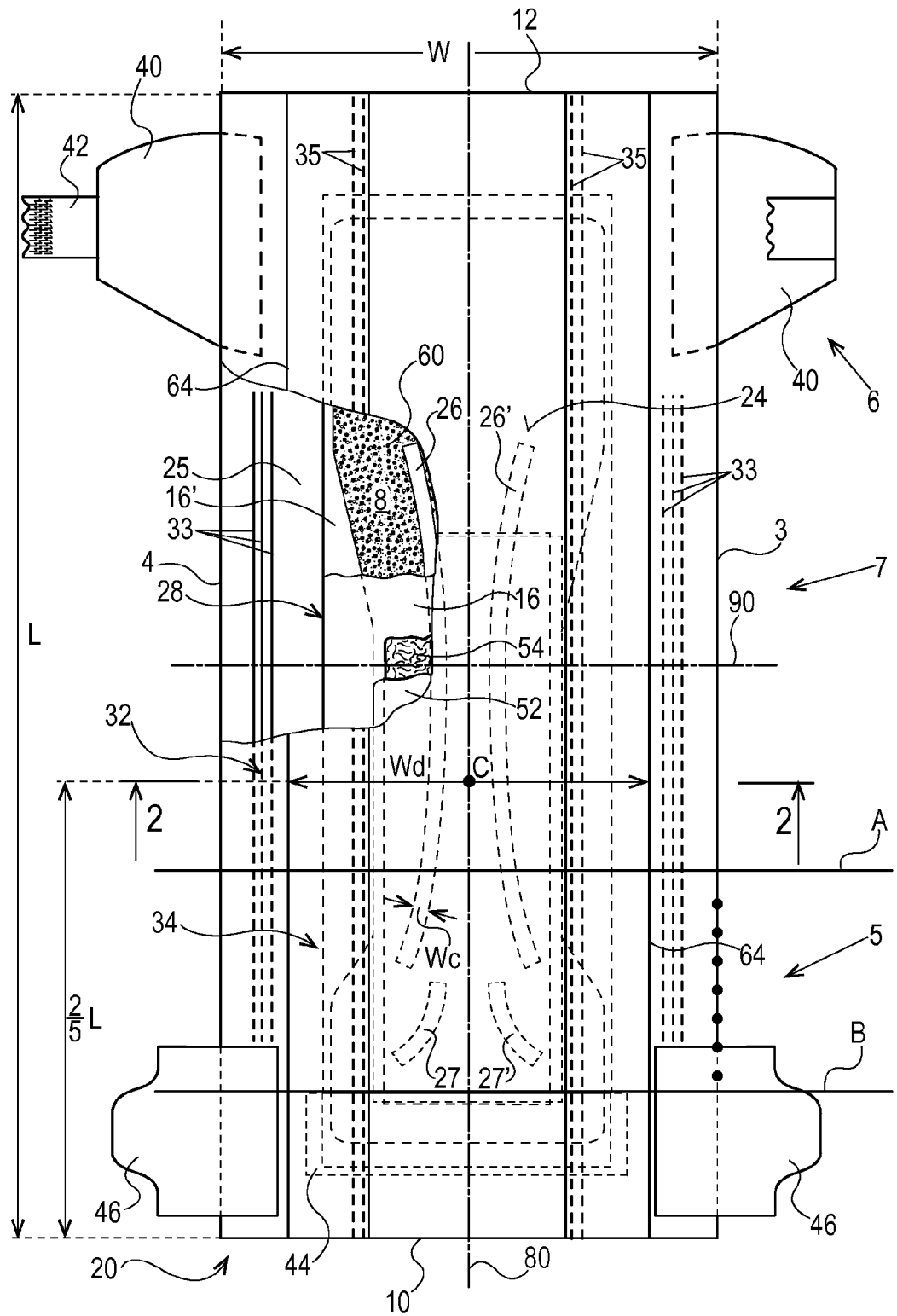
FIG. 1 is a top view of an absorbent article with some layers partially removed in accordance with a non-limiting embodiment of the present disclosure.

Various non-limiting embodiments of the present disclosure will now be described to provide an overall understanding of the principles of the structure, function, manufacture, and use of the absorbent articles with channel configurations and methods for making the same disclosed herein. One or more examples of these non-limiting embodiments are illustrated in the accompanying drawings. Those of ordinary skill in the art will understand that the absorbent articles with channel configurations and methods for making the same described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

Introduction

As used herein, the term "absorbent article" refers to disposable devices such as infant, child, or adult diapers, training pants, sanitary napkins, and the like which are placed against or in proximity to the body of the wearer to absorb and contain the various exudates discharged from the body. Typically, these articles comprise a topsheet, backsheet, an absorbent core, optionally an acquisition system (which may be comprised of one or several layers), and typically other components, with the absorbent core normally placed at least partially between the backsheet and the acquisition system or between the topsheet and the backsheet. The absorbent articles of the present disclosure will be further illustrated in the below description and in the Figures in the form of a taped diaper. Nothing in this description should be, however, considered limiting the scope of the claims. As such the present disclosure applies to any suitable form of absorbent articles (e.g., training pants, adult incontinence products, sanitary napkins).

A "nonwoven web" as used herein means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding, and airlaying. The basis weight of nonwoven webs is usually expressed in grams per square meter ($g/m^2$ or gsm).

The term "joined" or "bonded" or "attached", as used herein, encompasses configurations whereby an element is directly secured to another element by affixing the element directly to the other element, and configurations whereby an element is indirectly secured to another element by affixing the element to intermediate member(s) which in turn are affixed to the other element.

General Description of the Absorbent Article

Figure 2:
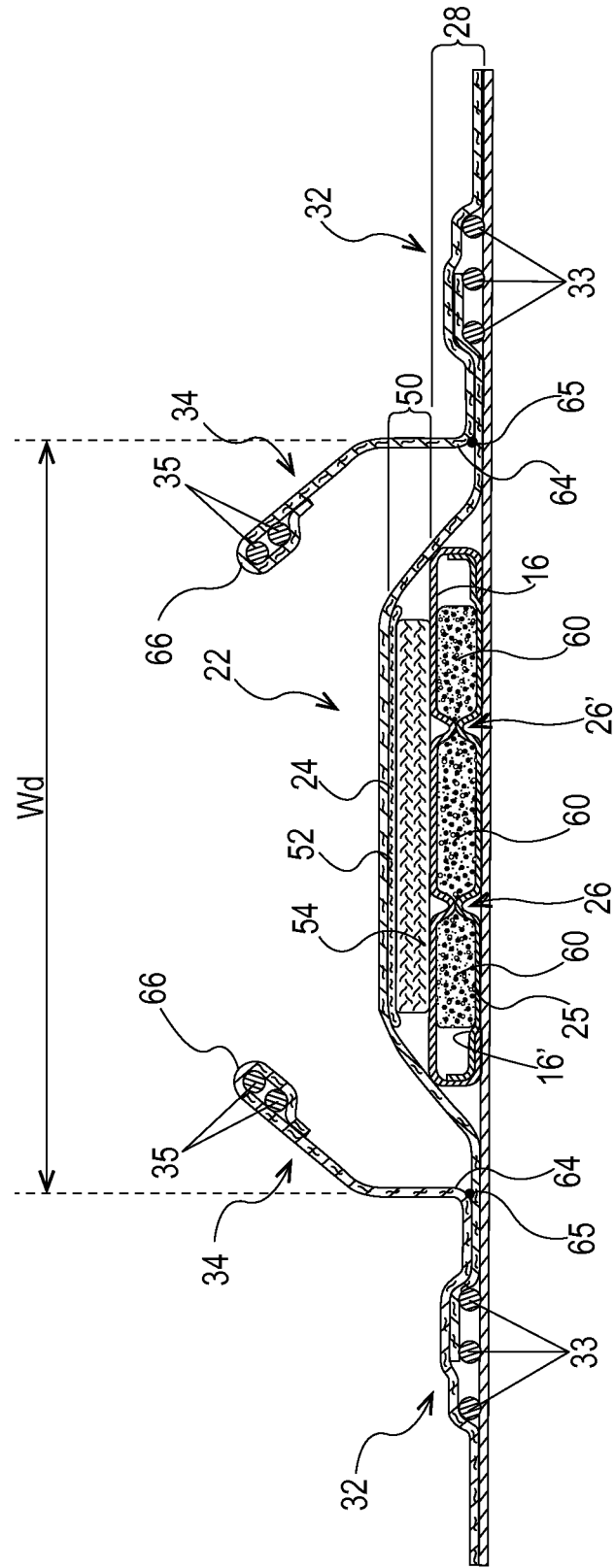
FIG. 2 is a cross-sectional view of the absorbent article taken about line 2-2 of FIG. 1 in accordance with a non-limiting embodiment of the present disclosure.
Figure 3:
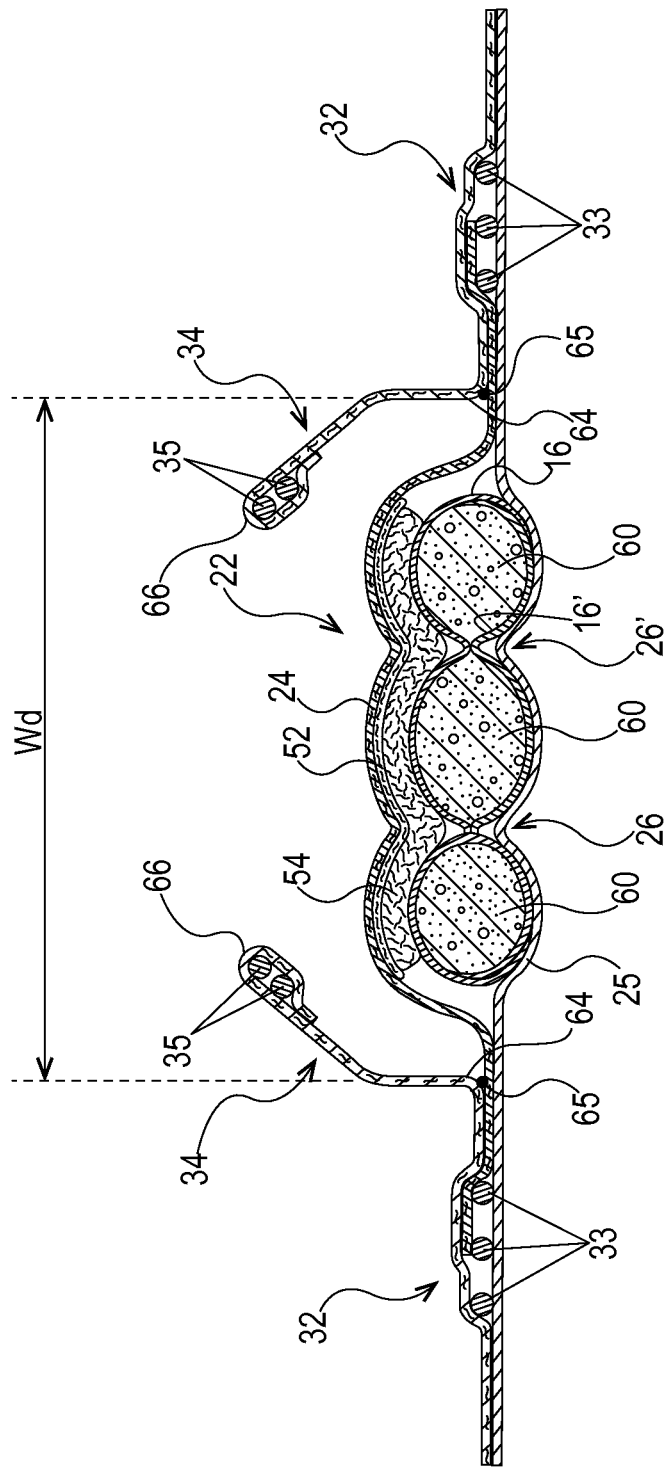
FIG. 3 is a view of the absorbent article of FIG. 2 where the absorbent article has been loaded with fluid in accordance with a non-limiting embodiment of the present disclosure.

An example absorbent article according to the present disclosure in the form of an infant diaper 20 is represented in FIGS. 1-3. FIG. 1 is a plan view of the example diaper 20, in a flat-out state, with portions of the structure being cut-away to more clearly show the construction of the diaper 20. This diaper 20 is shown for illustration purpose only as the present disclosure may be used for making a wide variety of diapers or other absorbent articles.

The absorbent article may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise an acquisition-distribution system ("ADS") 50, which in the example represented comprises a distribution layer 54 and an acquisition layer 52, which will be further detailed below. The absorbent article may also comprise elasticized gasketing cuffs 32 joined to the chassis of the absorbent article, typically via the topsheet and/or backsheet, and substantially planar with the chassis of the diaper.

The Figures also show typical taped diaper components such as a fastening system comprising adhesive tabs 42 attached towards the rear edge of the article and cooperating with a landing zone 44 on the front of the article. The absorbent article may also comprise other typical elements, which are not represented, such as a rear elastic waist feature, a front elastic waist feature, transverse barrier cuff(s), and/or a lotion application, for example.

The absorbent article 20 comprises a front waist edge 10, a rear waist edge 12 longitudinally opposing the front waist edge 10, a first side edge 3, and a second side edge 4 laterally opposing the first side edge 3. The front waist edge 10 is the edge of the article which is intended to be placed towards the front of the user when worn, and the rear waist edge 12 is the opposite edge. The absorbent article may have a longitudinal axis 80 extending from the lateral midpoint of the front waist edge 10 to a lateral midpoint of the rear waist edge 12 of the article and dividing the article in two substantially symmetrical halves relative to the longitudinal axis 80, with article placed flat and viewed from above as in FIG. 1. The absorbent article may also have a lateral axis 90 extending from the longitudinal midpoint of the first side edge 3 to the longitudinal midpoint of the second side edge 4. The length L of the article may be measured along the longitudinal axis 80 from the front waist edge 10 to the rear waist edge 12. The width of the article may be measured along the lateral axis 90 from the first side edge 3 to the second side edge 4. The article may comprise a crotch point C defined herein as the point placed on the longitudinal axis at a distance of two fifth (⅖) of L starting from the front edge 10 of the article 20. The article may comprise a front waist region 5, a rear waist region 6, and a crotch region 7. The front waist region, the rear waist region, and the crotch region each define ⅓ of the longitudinal length of the absorbent article.

The topsheet 24, the backsheet 25, the absorbent core 28, and the other article components may be assembled in a variety of configurations, in particular by gluing or heat embossing, for example. Example diaper configurations are described generally in U.S. Pat. Nos. 3,860,003, 5,221,274, 5,554,145, 5,569,234, 5,580,411, and 6,004,306. The absorbent article may be thin. The caliper at the crotch point C or in the crotch region 7 of the article may be, for example, from 4.0 mm to 12.0 mm or alternatively from 6.0 mm to 10.0 mm.

The absorbent core 28 may comprise an absorbent material comprising at least 80% by weight, at least 90% by weight, at least 95% by weight, or at least 99% by weight of superabsorbent polymers and a core wrap enclosing the superabsorbent polymers. The core wrap may typically comprise two materials, substrates, or nonwoven materials 16 and 16' for the top side and bottom side of the core. The core may comprises one or more channels, represented in FIG. 1 as the four channels 26, 26' and 27, 27'.

These and other components of the articles will now be discussed in more details.

Topsheet

The topsheet 24 is the part of the absorbent article that is directly in contact with the wearer's skin. The topsheet 24 can be joined to the backsheet 25, the core 28 and/or any other layers as is known to those of skill in the art. Usually, the topsheet 24 and the backsheet 25 are joined directly to each other in some locations (e.g., on or close to the periphery of the article) and are indirectly joined together in other locations by directly joining them to one or more other elements of the article 20.

The topsheet 24 may be compliant, soft-feeling, and non-irritating to the wearer's skin. Further, at least a portion of the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, Mass. under the designation P-8.

Suitable formed film topsheets are also described in U.S. Pat. Nos. 3,929,135, 4,324,246, 4,342,314, 4,463,045, and 5,006,394. Other suitable topsheets 30 may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, Va., as "CLIFF-T".

Any portion of the topsheet 24 may be coated with a lotion as is known in the art. Examples of suitable lotions include those described in U.S. Pat. Nos. 5,607,760, 5,609,587, 5,643,588, 5,968,025, and 6,716,441. The topsheet 24 may also include or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$ or between about 15 $cm^2$ and 35 $cm^2$. Examples of apertured topsheets are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 21 gsm or from about 12 to about 18 gsm, but other basis weights are within the scope of the present disclosure.

Backsheet

The backsheet 25 is generally that portion of the article 20 positioned adjacent the garment-facing surface of the absorbent core 28 and which prevents, or at least inhibits, the exudates absorbed and contained therein from soiling articles such as bedsheets and undergarments. The backsheet 25 is typically impermeable, or at least substantially impermeable, to liquids (e.g., urine). The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the diaper 20 while still preventing, or at least inhibiting, exudates from passing through the backsheet 25. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The backsheet 25 may be joined to the topsheet 24, the absorbent core 28, and/or any other element of the diaper 20 by any attachment methods known to those of skill in the art. Suitable attachment methods are described above with respect to methods for joining the topsheet 24 to other elements of the article 20. For example, the attachment methods may include using a uniform continuous layer of adhesive, a patterned layer of adhesive, or an array of separate lines, spirals, or spots of adhesive. Suitable attachment methods comprising an open pattern network of filaments of adhesive as disclosed in U.S. Pat. No. 4,573,986. Other suitable attachment methods include using several lines of adhesive filaments which are swirled into a spiral pattern, as is illustrated by the apparatus and methods shown in U.S. Pat. Nos. 3,911, 173, 4,785,996, and 4,842,666. Adhesives which have been found to be satisfactory are manufactured by H. B. Fuller Company of St. Paul, Minn. and marketed as HL-1620 and HL 1358-XZP. Alternatively, the attachment methods may comprise using heat bonds, pressure bonds, ultrasonic bonds, dynamic mechanical bonds, or any other suitable attachment methods or combinations of these attachment methods as are known to those of skill in the art.

Absorbent Core

As used herein, the term "absorbent core" refers to the individual component of the article having the most absorbent capacity and comprising an absorbent material and a core wrap enclosing the absorbent material. The term "absorbent core" does not include the acquisition-distribution system or layer or any other component of the article which is not either integral part of the core wrap or placed within the core wrap. The core may comprise, consist essentially of, or consist of, a core wrap, absorbent material as defined below, and glue enclosed within the core wrap.

The absorbent core 28 of the present disclosure may comprise an absorbent material with a high amount of superabsorbent polymers (herein abbreviated as "SAP") enclosed within a core wrap. The SAP content may represent 70%-100% or at least 70%, 75%, 80%, 85%, 90%, 95%, 99%, or 100% by weight of the absorbent material contained in the core wrap. The core wrap is not considered as absorbent material for the purpose of assessing the percentage of SAP in the absorbent core.

By "absorbent material" it is meant a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap. This provides a relatively thin core compared to conventional core typically comprising between 40-60% SAP and high content of cellulose fibers. The absorbent material may in particular comprises less than 15% or less than 10% weight percent of natural or synthetic fibers, less than 5% weight percent, less than 3% weight percent, less than 2% weight percent, less than 1% weight percent, or may even be substantially free of natural and/or synthetic fibers. The absorbent material may advantageously comprise little or no airfelt (cellulose) fibers, in particular the absorbent core may comprise less than 15%, 10%, 5%, 3%, 2%, 1% airfelt (cellulose) fibers by weight of the absorbent core, or may even be substantially free of cellulose fibers.

Figure 4:
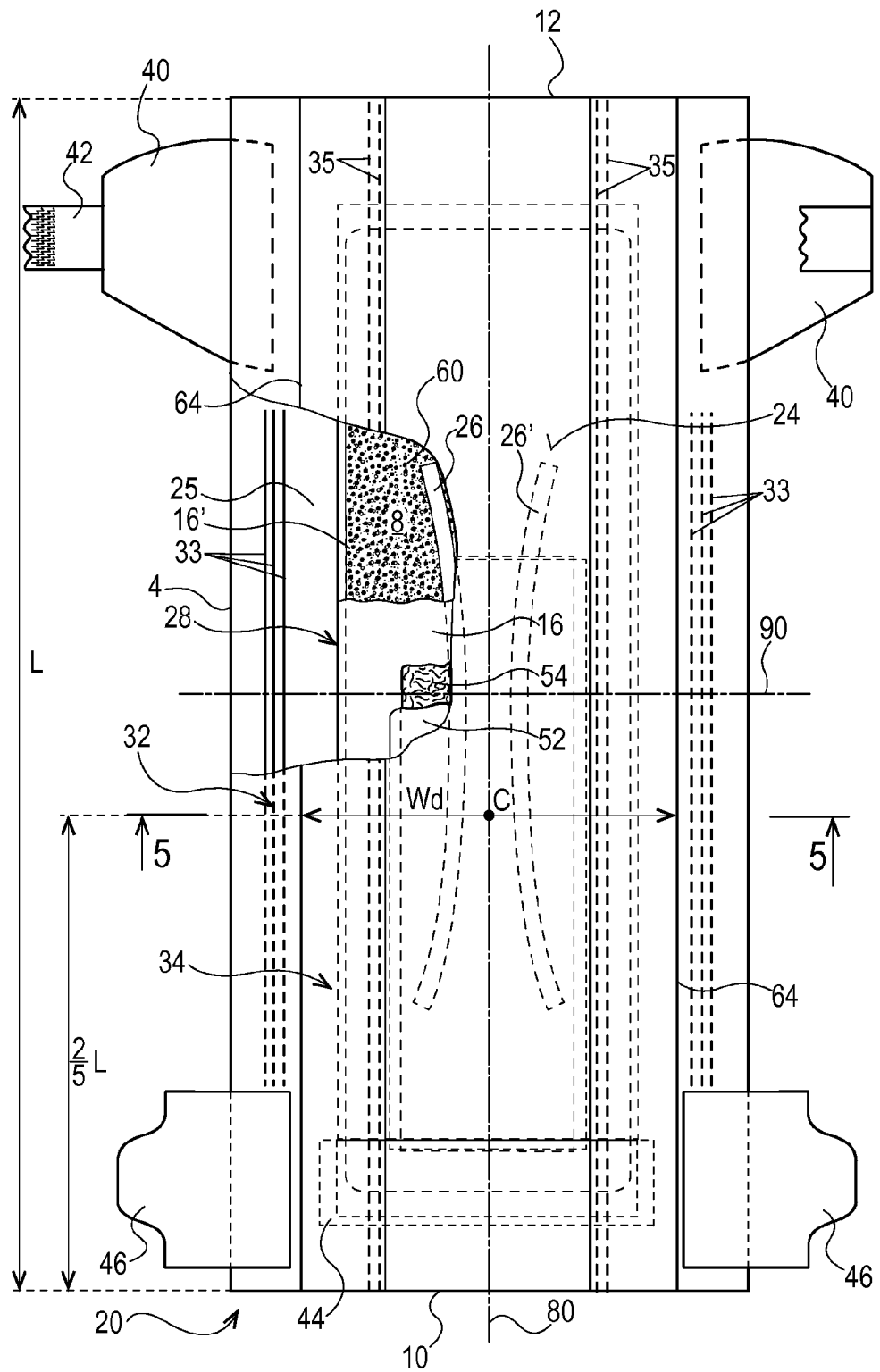
FIG. 4 is a top view of another absorbent article with some layers partially removed in accordance with a non-limiting embodiment of the present disclosure.
Figure 5:
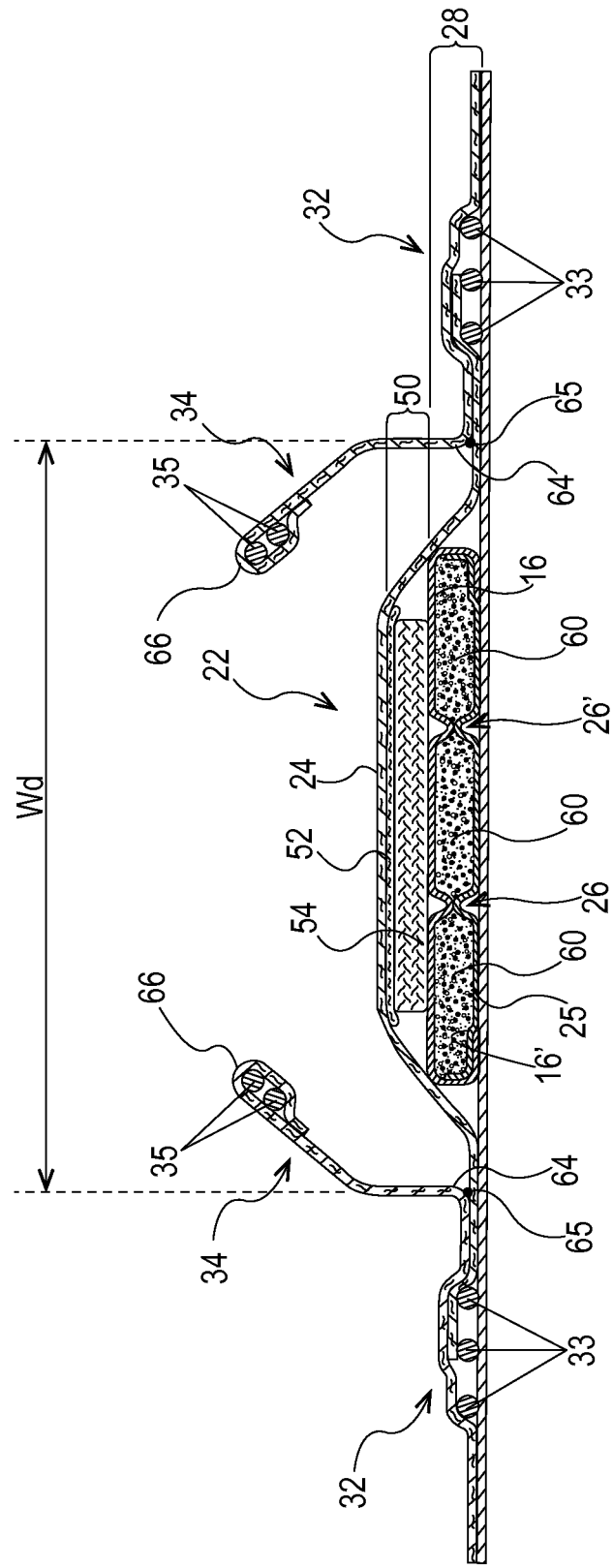
FIG. 5 is a cross-sectional view of the absorbent article taken about line 5-5 of FIG. 4 in accordance with a non-limiting embodiment of the present disclosure.
Figure 6:
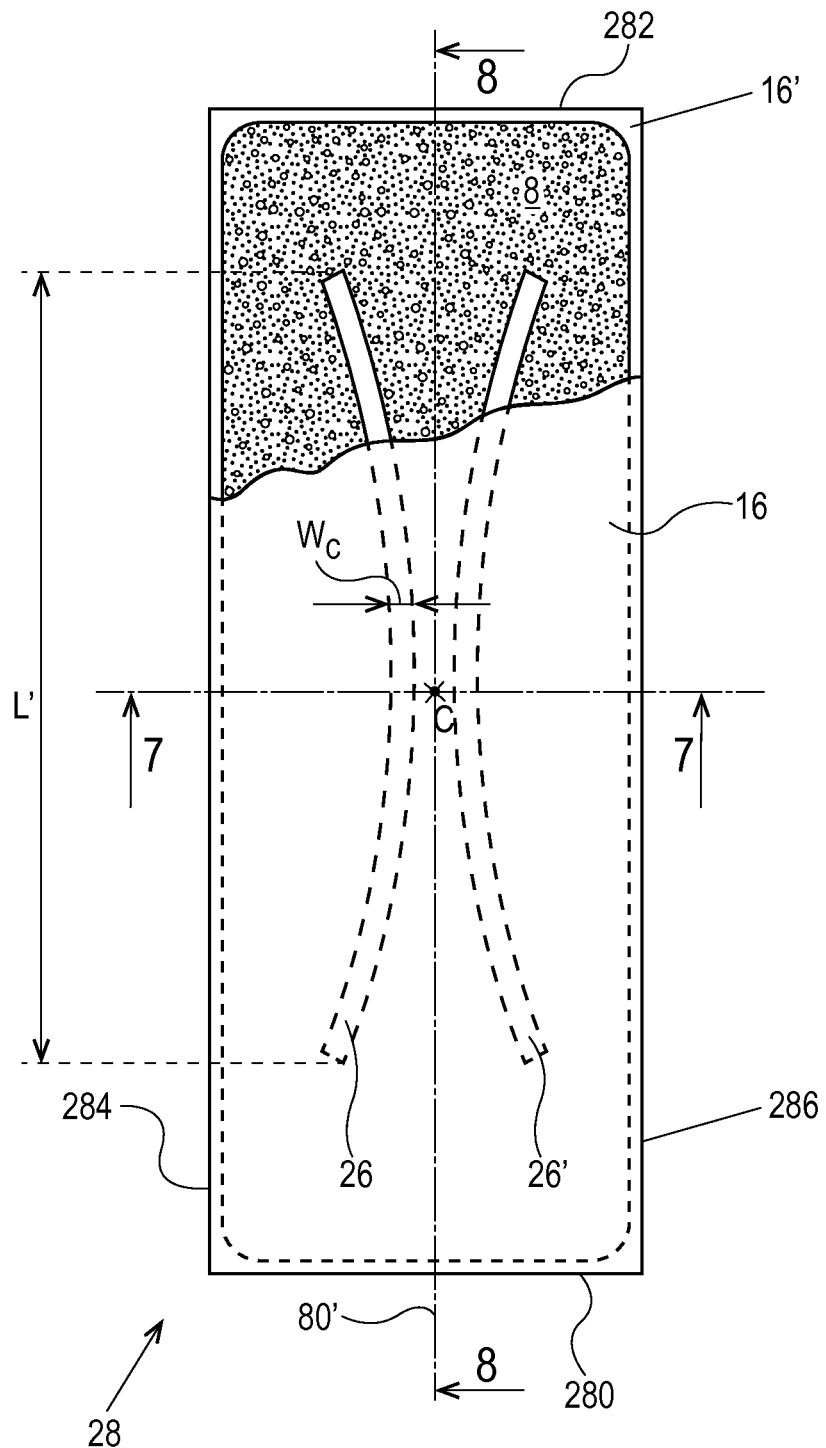
FIG. 6 is a top view of an absorbent core of the absorbent article of FIG. 4 with some layers partially removed in accordance with a non-limiting embodiment of the present disclosure.
Figure 7:
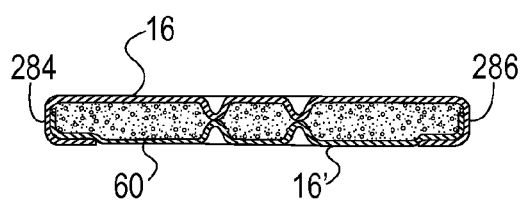
FIG. 7 is a cross-sectional view of the absorbent core taken about line 7-7 of FIG. 6 in accordance with a non-limiting embodiment of the present disclosure.
Figure 8:
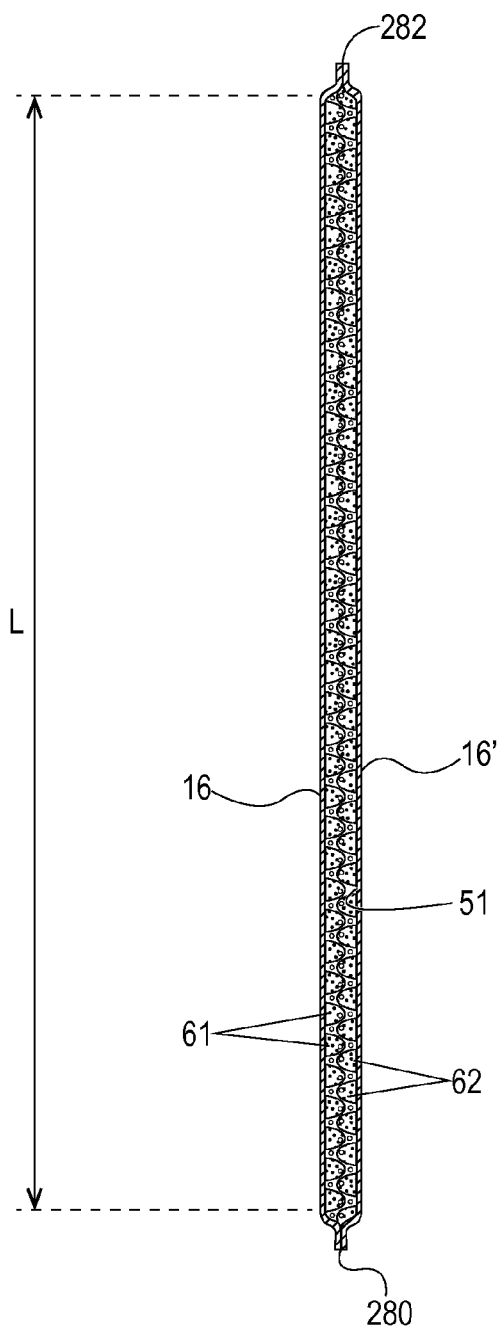
FIG. 8 is a cross-sectional view of the absorbent core taken about line 8-8 of FIG. 6 in accordance with a non-limiting embodiment of the present disclosure.

The example absorbent core 28 of the absorbent article of FIGS. 4-5 is shown in isolation in FIGS. 6-8. The absorbent core may comprises a front side 280, a rear side 282, and two longitudinal sides 284, 286 joining the front side 280 and the rear side 282. The absorbent core may also comprise a generally planar top side and a generally planar bottom side. The front side 280 of the core is the side of the core intended to be placed towards the front waist edge 10 of the absorbent article. The core 28 may have a longitudinal axis 80' corresponding substantially to the longitudinal axis 80 of the article, as seen from the top in a planar view as in FIG. 1. In an embodiment, the absorbent material may be distributed in higher amount towards the front side than towards the rear side as more absorbency may be required at the front in particular articles. In an embodiment, the front and rear sides of the core may be shorter than the longitudinal sides of the core. The core wrap may be formed by two nonwoven materials, substrates, laminates, or other materials, 16, 16' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 16 may at least partially surround the second material, substrate, or nonwoven 16' to form the core wrap, as illustrated in FIG. 7. The first material 16 may surround a portion of the second material 16' proximate to the first and second side edges 284 and 286.

The absorbent core of the present disclosure may comprise adhesive, for example, to help immobilizing the SAP within the core wrap and/or to ensure integrity of the core wrap, in particular when the core wrap is made of two or more substrates. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be a continuous layer present within the core wrap. In other embodiments, the absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two absorbent layers having discontinuous absorbent material application pattern, wherein the resulting layer is substantially continuously distributed across the absorbent particulate polymer material area, as disclosed in U.S. Pat. Appl. Pub. No. 2008/0312622A1 (Hundorf), for example. The absorbent core 28 may comprise a first absorbent layer and a second absorbent layer. The first absorbent layer may comprise the first material 16 and a first layer 61 of absorbent material, which may be 100% or less of SAP. The second absorbent layer may comprise the second material 16' and a second layer 62 of absorbent material, which may also be 100% or less of SAP. The absorbent core 28 may also comprise a fibrous thermoplastic adhesive material 51 at least partially bonding each layer of absorbent material 61, 62 to its respective material 16 or 16'. This is illustrated in FIGS. 7-8, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 80. The first material 16 and the second material 16' may form the core wrap.

The fibrous thermoplastic adhesive material 51 may be at least partially in contact with the absorbent material 61, 62 in the land areas and at least partially in contact with the materials 16 and 16' in the junction areas. This imparts an essentially three-dimensional structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The thermoplastic adhesive material 51 may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic adhesive used for the fibrous layer may have elastomeric properties, such that the web formed by the fibers on the SAP layer is able to be stretched as the SAP swell. Example elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 issued to Korpman on Mar. 15, 1988.

The thermoplastic adhesive material may be applied as fibers. The fibers may have an average thickness of about 1 to about 50 micrometers or about 1 to about 35 micrometers and an average length of about 5 mm to about 50 mm or about 5 mm to about 30 mm, specifically reciting all 0.1 micrometer increments within the above-specified ranges and any ranges formed therein or thereby. To improve the adhesion of the thermoplastic adhesive material to the materials 16 or 16' or to any other layer, in particular any other nonwoven layers, such layers may be pre-treated with an auxiliary adhesive. The fibers adhere to each other to form a fibrous layer, which can also be described as a mesh.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application Nos. WO 07/047,598, WO 07/046,052, WO2009/155265, and WO2009/155264, for example. In some embodiments, suitable superabsorbent polymer particles may be obtained by generally known production processes as described in WO 2006/083584, for example. The superabsorbent polymers may be internally cross-linked, i.e., the polymerization is carried out in the presence of compounds having two or more polymerizable groups which can be free-radically copolymerized into the polymer network. Useful crosslinkers include, for example, ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301, and in DE-A 103 31 450, mixed acrylates which, as well as acrylate groups, include further ethylenically unsaturated groups, as described in DE-A 103 31 456 and DE-A 103 55 401, or crosslinker mixtures as described, for example, in DE-A 195 43 368, DE-A 196 46 484, WO 90/15830, and WO 02/32962 as well as cross-linkers described in WO2009/155265. The superabsorbent polymer particles may be external surface cross-linked, or post cross-linked. Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019, cyclic carbonates as described in DE-A 40 20 780, 2-oxazolidone and its derivatives, such as N-(2-hydroxyethyl)-2-oxazolidone as described in DE-A 198 07 502, bis- and poly-2-oxazolidones as described in DE-A 198 07 992, 2-oxotetrahydro-1,3-oxazine and its derivatives as described in DE-A 198 54 573, N-acyl-2-oxazolidones as described in DE-A 198 54 574, cyclic ureas as described in DE-A 102 04 937, bicyclic amide acetals as described in DE-A 103 34 584, oxetane and cyclic ureas as described in EP1,199,327 and morpholine-2,3-dione and its derivatives as described in WO03/031482.

In some embodiments, the SAP may be formed from polyacrylic acid polymers or polyacrylate polymers, for example, having a neutralization degree of from 60% to 90%, or of about 75%, having, for example, sodium counter ions.

The SAP useful for the present disclosure may be of numerous shapes. The term "particles" refers to granules, fibers, flakes, spheres, powders, platelets and other shapes and forms known to persons skilled in the art of superabsorbent polymer particles. In some embodiments, the SAP particles can be in the shape of fibers, i.e., elongated, acicular superabsorbent polymer particles. In those embodiments, the superabsorbent polymer particles fibers may have a minor dimension (i.e., diameter of the fiber) of less than about 1 mm, usually less than about 500 µm, or less than 250 µm down to 50 µm, specifically reciting all 1 µm increments within the above-specified ranges and any ranges formed therein or thereby. The length of the fibers may be about 3 mm to about 100 mm, specifically reciting all 1 mm increments within the above-specified range and any ranges formed therein or thereby. The fibers may also be in the form of a long filament that may be woven.

SAP may be spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 µm, from 50 to 850 µm, from 100 to 710 µm, or from 150 to 650 µm, specifically reciting all 1 µm increments within the above-specified ranges and any ranges formed therein or thereby, as measured according to EDANA method WSP 220.2-05. SAP having a relatively low particle size may help to increase the surface area of the absorbent material which is in contact with liquid exudates and therefore supports fast absorption of liquid exudates.

The SAP may have a particle sizes in the range from 45 µm to 4000 µm, more specifically a particle size distribution within the range of from 45 µm to about 2000 µm, or from about 100 µm to about 1000, 850 or 600 µm, specifically reciting all 1 µm increments within the above-specified ranges and any ranges formed therein or thereby. The particle size distribution of a material in particulate form can be determined, for example, by means of dry sieve analysis (EDANA 420.02 "Particle Size distribution).

In some embodiments herein, the superabsorbent material may be in the form of particles with a mass medium particle size up to 2 mm, between 50 microns and 2 mm or to 1 mm, or from 100 µm, 200 µm, 300 µm, 400 µm, 500 µm, 1000 µm, 800 µm, or 700 µm; as can, for example, be measured by the method set out in for example EP-A-0,691,133. In some embodiments of the present disclosure, the superabsorbent polymer material is in the form of particles whereby at least 80% by weight are particles of a size between 50 µm and 1200 µm and having a mass median particle size between any of the range combinations above. In addition, or in another embodiment of the present disclosure, the particles may be essentially spherical. In yet another or additional embodiment of the present disclosure, the superabsorbent polymer material may have a relatively narrow range of particle sizes, e.g., with the majority (e.g., at least 80%, at least 90%, at least 95%, or even at least 99% by weight) of particles having a particle size between 50 µm and 1000 µm, between 100 µm and 800 µm, or between 200 µm and 600 µm, specifically reciting all 1 µm increments within the above-specified ranges and any ranges formed therein or thereby.

The surface of the SAP may be coated, for example, with a cationic polymer. Certain cationic polymers may include polyamine or polyimine materials. In some embodiments, the SAP may be coated with chitosan materials such as those disclosed in U.S. Pat. No. 7,537,832 B2. In some other embodiments, the SAP may comprise mixed-bed Ion-Exchange absorbent polymers such as those disclosed in WO 99/34841 and WO 99/34842.

The absorbent core may comprise one or more types of SAP.

For most absorbent articles, liquid discharges from a wearer occur predominately in the front half of the article, in particular for a diaper. The front half of the article (as defined by the region between the front edge and a transversal line placed at a distance of half L from the front waist edge 10 or rear waist edge 12 may therefore comprise most of the absorbent capacity of the core. Thus, at least 60% of the SAP, or at least 65%, 70%, 75%, 80%, or 85% of the SAP may be present in the front half of the absorbent article, the remaining SAP being disposed in the rear half of the absorbent article. In other embodiments, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m². The areas of the channels (e.g., 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 2 and 7, the longitudinal and/or transversal edges of one of the substrates are folded over the other substrate to form flaps. These flaps are then bonded to the external surface of the other substrate, typically by gluing.

The core wrap may be formed by any materials suitable for receiving and containing the absorbent material. Typical substrate materials used in the production of conventional cores may be used, in particular paper, tissues, films, wovens or nonwovens, or laminates or composites of any of these. The core wrap may be formed by a nonwoven web, such as a carded nonwoven, spunbond nonwoven ("S") or meltblown nonwoven ("M"), and laminates of any of these. For example, spunmelt polypropylene nonwovens may be suitable, in particular those having a laminate web SMS, or SMMS, or SSMMS, structure, and having a basis weight range of about 5 gsm to about 15 gsm. Suitable materials are disclosed in U.S. Pat. No. 7,744,576, U.S. Pat. Publ. No. 2011/0268932A1, U.S. Pat. Publ. No. 2011/0319848A1, and U.S. Pat. Publ. No. 2011/0250413A1. Nonwoven materials provided from synthetic fibers may also be used, such as PE, PET, and/or PP, for example.

If the core wrap comprises a first substrate, nonwoven or material 16 and a second substrate, nonwoven, or materials 16' these may be made of the same type of material, may be made of different materials, or one of the substrates may be treated differently than the other to provide it with different properties. As the polymers used for nonwoven production are inherently hydrophobic, they may be coated with hydrophilic coatings if placed on the fluid receiving side of the absorbent core. It may be advantageous that the top side of the core wrap, i.e., the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g., as described in WO 02/064877.

Permanently hydrophilic nonwovens are also useful in some embodiments. Surface tension, as described in U.S. Pat. No. 7,744,576 (Busam et al.), can be used to measure how permanently a certain hydrophilicity level is achieved. Liquid strike through, as described in U.S. Pat. No. 7,744,576, may be used to measure the hydrophilicity level. The first and/or second substrate may have a surface tension of at least 55, at least 60, or at least 65 mN/m or higher when wetted with saline solution. The substrate may also have a liquid strike through time of less than 5 seconds for a fifth gush of liquid. These values can be measured using the test methods described in U.S. Pat. No. 7,744,576B2: "Determination Of Surface Tension" and "Determination of Strike Through" respectively.

Hydrophilicity and wettability are typically defined in terms of contact angle and the strike through time of the fluids, for example, through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have an air-permeability of from 40 or from 50, to 300 or to 200 m$^3$/(m$^2$×min), as determined by EDANA method 140-1-99 (125 Pa, 38.3 cm$^2$). The material of the core wrap may alternatively have a lower air-permeability, e.g., being non-air-permeable, for example, to facilitate handling on a moving surface comprising vacuum.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an embodiment, neither the first nor the second substrates need to be shaped, so that they can be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may thus have a width (as measured in the transversal direction) at its narrowest point which is less than about 100 mm, 90 mm, 80 mm, 70 mm, 60 mm, or even less than about 50 mm. This narrowest width may further be at least 5 mm, or at least 10 mm, smaller than the width of the deposition area 8 at its largest point in the front and/or rear regions deposition area 8. The absorbent material deposition area 8 may also be generally rectangular, for example as shown in FIGS. 4-6, but other deposition areas, such as a "T," "Y," "sand-hour," or "dog-bone" shapes are also within the scope of the present disclosure.

The basis weight (amount deposited per unit of surface) of the SAP may also be varied along the deposition area 8 to create a profiled distribution of absorbent material, in particular SAP, in the longitudinal direction, in the transversal direction, or both directions of the core. Hence, along the longitudinal axis of the core, the basis weight of absorbent material may vary, as well as along the transversal axis, or any axis parallel to any of these axes. The basis weight of SAP in areas of relatively high basis weight may thus be at least 10%, 20%, 30%, 40%, or 50% higher than in an area of relatively low basis weight. In one embodiment, the SAP present in the absorbent material deposition area 8 at the level of the crotch point C may have more SAP per unit of surface deposited as compared to another area of the absorbent material deposition area 8.

The absorbent material may be deposited using known techniques, which may allow relatively precise deposition of SAP at relatively high speed. In particular, the SAP printing technology as disclosed in U.S. Pat. Publ. No. 2008/0312617 and U.S. Pat. Publ. No. 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core may be formed for example by modifying the pattern of the grid and receiving drums so that no SAP is applied in areas corresponding to the channels. EP application number 11169396.6 discloses this modification in more details.

Channels

The absorbent material deposition area 8 may comprise at least one channel 26, which is at least partially oriented in the longitudinal direction of the article 80 (i.e., has a longitudinal vector component). Other channels may be at least partially oriented in the lateral direction (i.e., has a lateral vector component) or in any other direction. If the following, the plural form "channels" will be used to mean "at least one channel". The channels may have a length L' projected on the longitudinal axis 80 of the article that is at least 10% of the length L of the article. The channels may be formed in various ways. For example, the channels may be formed by zones within the absorbent material deposition area 8 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The acquisition-distribution system or layer 50, or another layer of the article, may also comprise channels, which may or not correspond to the channels of the absorbent core.

In some embodiments, the channels may be present at least at the same longitudinal level as the crotch point C or the lateral axis 60 in the absorbent article, as represented in FIG.

1 with the two longitudinally extending channels 26, 26'. The channels may also extend from the crotch region 7 or may be present in the front waist region 5 and/or in the rear waist region 6 of the article.

The absorbent core 28 may also comprise more than two channels, for example, at least 3, at least 4, at least 5, or at least 6 or more. Shorter channels may also be present, for example in the rear waist region 6 or the front waist region 5 of the core as represented by the pair of channels 27, 27' in FIG. 1 towards the front of the article. The channels may comprise one or more pairs of channels symmetrically arranged, or otherwise arranged relative to the longitudinal axis 80.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may extend substantially longitudinally, which means that each channel extends more in the longitudinal direction than in the transverse direction, or at least twice as much in the longitudinal direction than in the transverse direction (as measured after projection on the respective axis). In other embodiments, the channels may extend substantially laterally, which means that each channel extends more in the lateral direction than in the transverse direction, or at least twice as much in the longitudinal direction than in the transverse direction (as measured after projection on the respective axis).

The channels may be completely oriented longitudinally and parallel to the longitudinal axis or completely oriented transversely and parallel to the lateral axis, but also may be curved. In various embodiments, some or all the channels, in particular the channels present in the crotch region 7, may be concave towards the longitudinal axis 80, as, for example, represented in FIG. 1 for the pair of channels 26, 26'. The radius of curvature may typically be at least equal (and may be at least 1.5 or at least 2.0 times this average transverse dimension) to the average transverse dimension of the absorbent layer; and also straight but under an angle of (e.g., from 5°) up to 30°, up to 20°, up to 10° with a line parallel to the longitudinal axis. The radius of curvature may be constant for a channel, or may vary along its length. This may also include channels with an angle therein, provided the angle between two parts of a channel is at least 120°, at least 150°; and in any of these cases, provided the longitudinal extension of the channel is more than the transverse extension. The channels may also be branched. For example, a central channel superposed with the longitudinal axis in the crotch region 7 which branches towards the rear waist edge 12 and/or towards the front waist edge 10 of the article.

In some embodiments, there is no channel that coincides with the longitudinal axis 80 of the article or the core. When present as symmetrical pairs relative to the longitudinal axis 80, the channels may be spaced apart from one another over their whole longitudinal dimension. The smallest spacing distance may be at least 5 mm, at least 10 mm, or at least 16 mm, for example.

Furthermore, in order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width We along at least part of its length which is at least 2 mm, at least 3 mm, at least 4 mm, up to for example 20 mm, 16 mm, or 12 mm, for example. The width of the channel may be constant through substantially the whole length of the channel or may vary along its length. When the channels are formed by absorbent material-free zone within the absorbent material deposition area 8, the width of the channels is considered to be the width of the material free zone, disregarding the possible presence of the core wrap within the channels. If the channels are not formed by absorbent material free zones, for example mainly though bonding of the core wrap through the absorbent material zone, the width of the channels if the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. Typically, an adhesive may be used to bond both sides of the core wrap or the topsheet and the a backsheet through the channels, but it is possible to bond via other known processes, such as pressure bonding, ultrasonic bonding, heat bonding, or combination thereof. The core wrap or the topsheet 24 and the backsheet 25 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Figure 9:
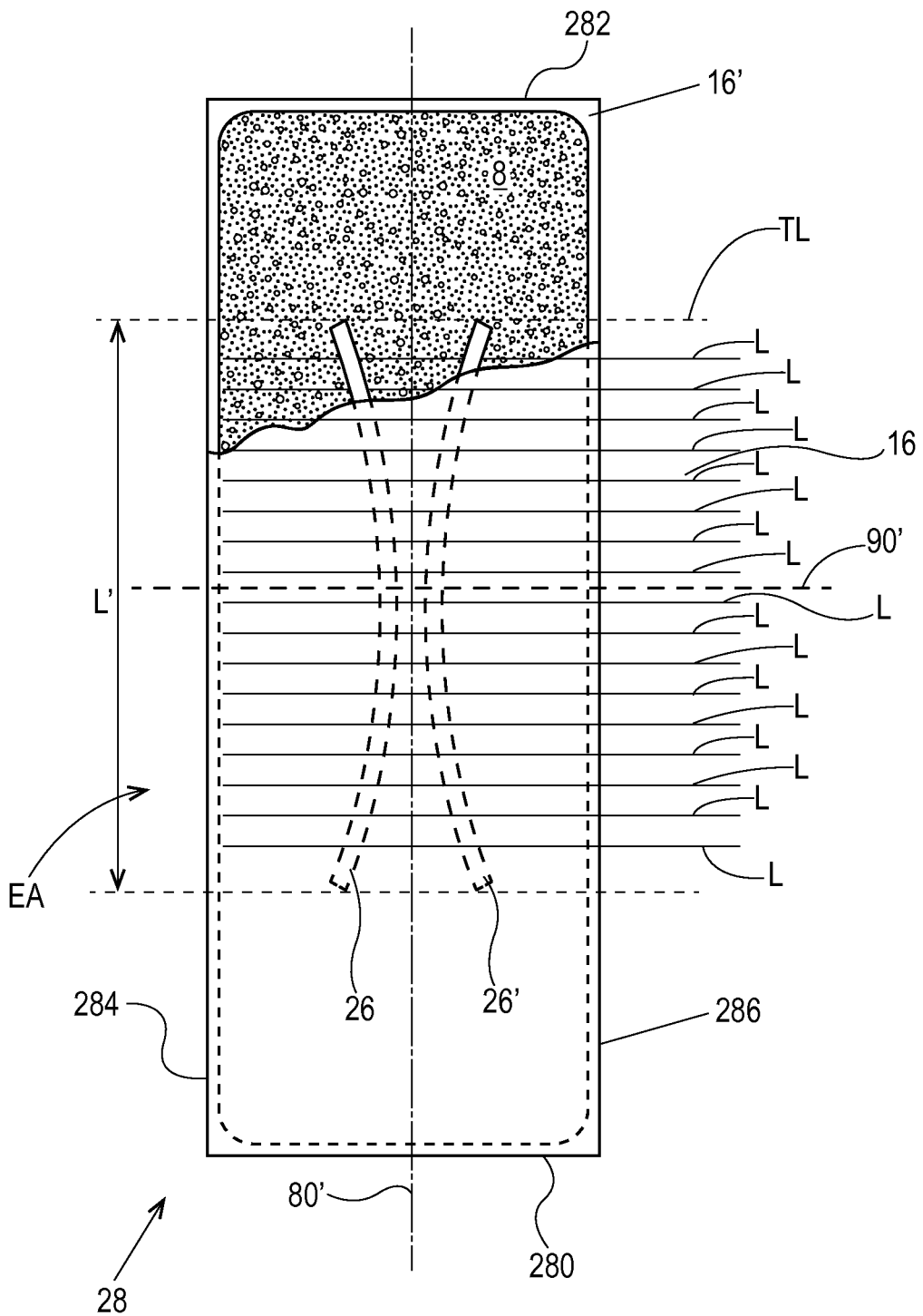
FIG. 9 is a top view of an absorbent core for an absorbent article in accordance with a non-limiting embodiment of the present disclosure.

FIG. 9 illustrates an example absorbent core 28 of the present disclosure. This core 28, and the cores illustrated in FIGS. 12 and 14-20, may be used in the absorbent articles of the present disclosure and may have many or all of the features discussed herein. In various embodiments, profiles of the sum of the lateral widths of one or more channels (plotted on the Y-axis) may be plotted relative to the longitudinal length about the longitudinal axis 80' (plotted on the X-axis) of portions of the one or more channels. Stated another way, the sum of the lateral widths of the one or more channels over a particular a longitudinal length about the longitudinal axis 80' of the one or more channels may be plotted to create a profile.

To obtain data for such profiles, first, the absorbent article or the absorbent core should be placed on a light table or a light source suitable for viewing the channels within the absorbent core. If the absorbent core is being used, it should first be removed from the absorbent article using any suitable techniques. The wearer-facing surface of the absorbent article or the absorbent core should face away from the surface of the light table. The absorbent article or the absorbent core should be attached to the light illuminating surface of the light table or light source using tape or other attachment members. Second, a longitudinal length along the longitudinal axis 80 or 80' (e.g., 5 mm, 10 mm, 15 mm, 20 mm, 50 mm, 100 mm) should be selected for measurement. A rigid or flexible tape measure, graduated in mm, should be used to measure the longitudinal length along the longitudinal axis 80 or 80'. A dot should be placed on the absorbent article or the absorbent core at either end of the longitudinal length on the longitudinal axis 80 or 80'. Next, a line that is parallel to the lateral axis 90' should be drawn through each dot. This enclosed area "EA" between the lines is the area to be measured. The enclosed area "EA" can be a portion of the absorbent article's or absorbent core's longitudinal length or the entire length of the absorbent article or absorbent core from the front waist edge 10 or front side 280 to the rear waist edge 12 or rear side 282, respectively. In some instances, it may be desirable to profile a large longitudinal length of the absorbent article or absorbent core, while, in other instances, it may be desirable to profile a small longitudinal length. Once the longitudinal length to be used is indicated on the absorbent article or the absorbent core, the sum of the lateral widths of the channels within the enclosed area should be measured parallel to the lateral axis every 5 mm along the longitudinal length using the tape measure. If only one channel is present at a particular 5 mm increment within the enclosed area "EA" only one width will be the sum of the lateral widths of the channel at that particular increment, while if more than one channel is present at a particular 5 mm increment within the enclosed area "EA", the sum of the lateral widths at that increment will be the sum of those two or more lateral widths of the channels. Those results should then be plotted to create a profile or graph with the sum of the lateral widths of the one or more channels being plotted on the Y-axis and the longitudinal length along the longitudinal axis 80 or 80' at which they were taken on the X-axis. The X-axis should be graduated in 5 mm increments to correspond with lateral width measurements being taken every 5 mm along the longitudinal axis 80 or 80'. The Y-axis may be graduated in 1 mm increments, 2 mm increments, or greater than 2 mm increments depending on the values of the sum of the lateral widths of the one or more channels.

Figure 10:
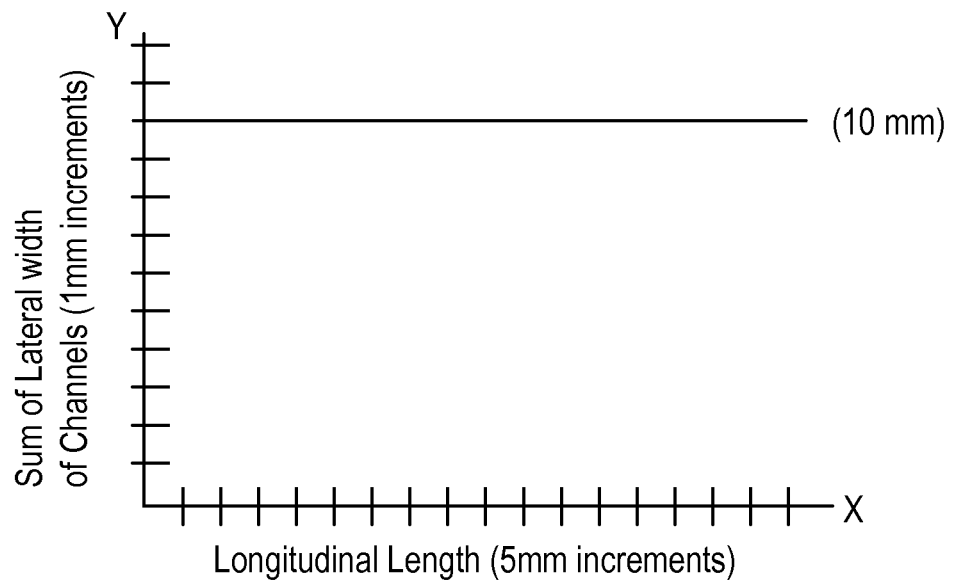
FIG. 10 is a profile of the sum of the lateral widths of two channels of FIG. 9 graphed against the longitudinal length of the channels within the enclosed area "EA" in accordance with a non-limiting embodiment of the present disclosure.

Referring to FIG. 9, as an example, the enclosed area "EA" is between the two dashed lines at the end of the longitudinal length L' of the one or more channels along the longitudinal axis 80'. For all absorbent core 28 embodiments, the longitudinal axis 80' corresponds with the longitudinal axis 80 of the absorbent article and the lateral axis 90' corresponds with the lateral axis 90 of the absorbent article. Lateral width measurements of the channels 26 and 26' are taken parallel to the lateral axis 90' every 5 mm. Each 5 mm increment is indicated as a line "L" in FIG. 9. The first measurement is taken 5 mm into the enclosed area "EA" from the top dashed line "TL". While FIG. 9 is not to scale, a profile of the sum of the lateral widths taken in a direction parallel to the lateral axis 90' every 5 mm along the longitudinal axis 80' would look generally like the example profile of FIG. 10. The longitudinal length along the longitudinal axis 80 is plotted on the X-axis and the sum of the lateral widths is plotted on the Y-axis. In this example, the sums of the laterals widths of the channels within the enclosed area (every 5 mm) are all 10 mm (5 mm per channel). Other sums of the lateral widths of the channels are within the scope of the present disclosure. Example sums of the lateral widths may be in the range of 5 mm to 120 mm, specifically reciting all 1 mm increments within the specified range and any ranges formed therein or thereby. The enclosed area may extend at least 5 mm, at least 10 mm, at least 15 mm, at least 20 mm, at least 30 mm, at least 40 mm, at least 50 mm, at least 60 mm, or at least 70 mm, for example, along the longitudinal axis 90'. The enclosed area may be smaller for sanitary napkins since their absorbent cores are typically smaller than diapers. Thus, the profile from FIG. 9 is constant, or substantially constant, since the sum of the lateral widths of the channels 26 and 26' taken every 5 mm along the longitudinal axis 80' should have the same value. If only channel 26 were present in the enclosed area of FIG. 9, the profile would also be constant, or substantially constant, since the lateral width of the channel 26 measured parallel to the lateral axis 90' is constant, or substantially constant, in this embodiment along the longitudinal length L'. The second channel 26' may be positioned on the opposite side of the longitudinal axis 80' as the first channel 26. The profile of the second channel 26' may also be constant, or substantially constant, about a longitudinal length, such as L' of FIG. 9, since the lateral width of the second channel 26' is constant, or substantially constant, about the channel's longitudinal length L'. In other embodiments, the lateral widths of each channel 26 and 26' may be constant, substantially constant, or variable along a longitudinal length or a portion thereof. In other embodiments, one channel (e.g., channel 26) may have a constant, or substantially constant, lateral width about its longitudinal length, while the other channel (e.g., channel 26') may have a varying lateral width about its longitudinal length. In the embodiment of FIG. 9, the channel 26 and the channel 26' may have the same longitudinal length along the longitudinal axis 80'. In other embodiments, the first and second or more channels may each have a different longitudinal length along the longitudinal axis 80'.

The above is merely an example non-limiting configuration of how to measure the sum of the lateral widths over a particular longitudinal length along the longitudinal axis 80'. As discussed below, other profiles are also within the scope of the present disclosure based on the configurations and/or orientations of the channels within the measured longitudinal length and/or enclosed area.

Again referring to FIG. 9, a profile of the sum of the lateral widths of the channels 26 and 26' over a portion of the longitudinal length on a first side of the lateral axis 90' may be different than a profile of the sum of the lateral widths of the channels 26 and 26' over another portion of the longitudinal length on a second side of the lateral axis 90'. In other embodiments, the profile of the sum of the lateral widths of the channels 26 and 26' over a portion of the longitudinal length on the first side of the lateral axis 90' may be the same, or substantially the same, as the profile of the sum of the lateral widths of the channels 26 and 26' over a portion of the longitudinal length on the second side of the lateral axis 90'

In an embodiment, referring to FIG. 1, the absorbent core 28 may comprise at least three channels or four channels (e.g., 26, 26', 27, 27'). These channels may be free of, or substantially free of (e.g., less than 10%, less than 5%, less than 3%, less than 2%, or less than 1%), superabsorbent polymers and may be at least partially oriented in the longitudinal direction and/or may be at least partially oriented in the lateral direction. In various embodiments, the longitudinal lengths of the channels 26 and 26' about the longitudinal axis 80 may be the same, substantially the same (e.g., within 2 mm or less of each other), or different and the longitudinal lengths of the channels 27 and 27' about the longitudinal axis 80 may be the same, substantially the same, or different. The longitudinal length of the channels 26 and 26' may be larger than the longitudinal length of the channels 27 and 27'. The average lateral width over the longitudinal lengths of the channels 27 and 27' may be the same, substantially the same, or may be different. Likewise, the average lateral width over the longitudinal lengths of the channels 26 and 26' may be the same, substantially the same, or may be different. The average lateral width of any of the channels 26, 26', 27, and 27' may be the same, substantially the same, or different. This rationale may apply to any channel configurations disclosed herein.

In an embodiment, referring again to FIG. 1, at least two of the three channels 26, 26', 27, and 27' may be at least partially oriented in the longitudinal direction along of the longitudinal axis 80 of the article. Each of the channels 26, 26', 27, and 27' may have lateral widths taken parallel to the lateral axis 90.

Figure 11:
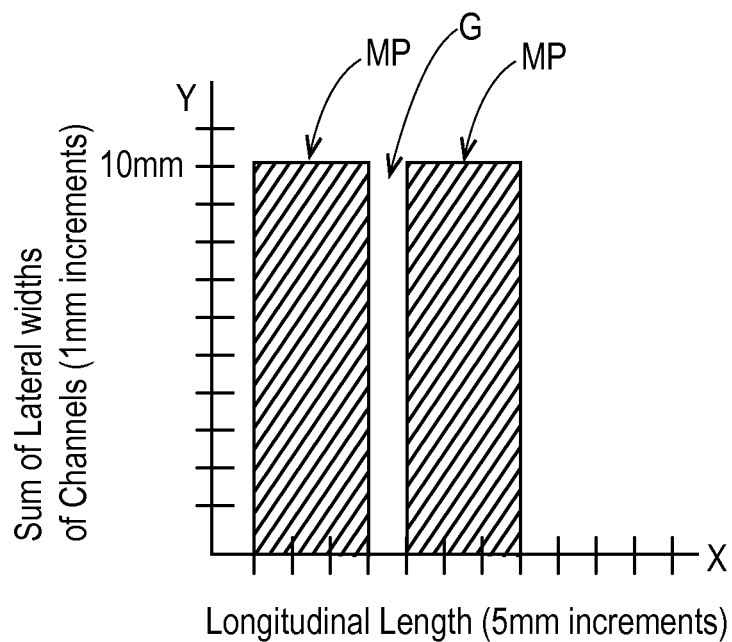
FIG. 11 is a profile of the sum of the lateral widths of portions of the channels of FIG. 1 graphed against the longitudinal length of the channels between lines A and B of FIG. 1 in accordance with a non-limiting embodiment of the present disclosure.

Referring to FIG. 11, a profile of the sum of the lateral widths of the channels over a longitudinal length along the longitudinal axis 80 of at least 5 mm, at least 10 mm, at least 15 mm, at least 20 mm, at least 25 mm, at least 30 mm, at least 35 mm, at least 40 mm, at least 45 mm, at least 50 mm or greater taken along the longitudinal axis 80 may have two maximum peaks "MP." The maximum peaks may be separated from each other by a gap "G" extending at least 1 mm, at least 3 mm, at least 5 mm, at least 10 mm, at least 15 mm, at least 20 mm or greater of the longitudinal length about the longitudinal axis 80. An example of such a profile is illustrated in FIG. 11. The profile of FIG. 11 was taken between the longitudinal length represented by lines A and B every 5 mm in longitudinal length (represented by dots along the first side edge 3). Lines parallel to the lateral axis 90 and intersecting each dot should be drawn on the absorbent article. The sum of the lateral width of the channels taken parallel to the lateral axis 90 should be measured on each line using the tape measure. Although the maximum peaks "MP" of FIG. 11 are illustrated separated by a 5 mm gap "G", this gap could be less than 1 mm or greater than 1 mm, for example, 1-15 mm or 1-9 mm.

Again referring to FIG. 11, the profile of the sum of the lateral widths of the channels 26, 26', 27, and/or 27' over a longitudinal length of at least 20 mm taken along the longitudinal axis 80 may be bimodal and may have a portion between the two modes where the sum of the lateral widths of at least three of the channels 26, 26', 27, and 27' or all of the channels is zero. This portion where the sum of the lateral widths of at least three of the channels 26, 26', 27, and 27' or all of the channels is zero is indicated by the gap G in FIG. 11.

Figure 12:
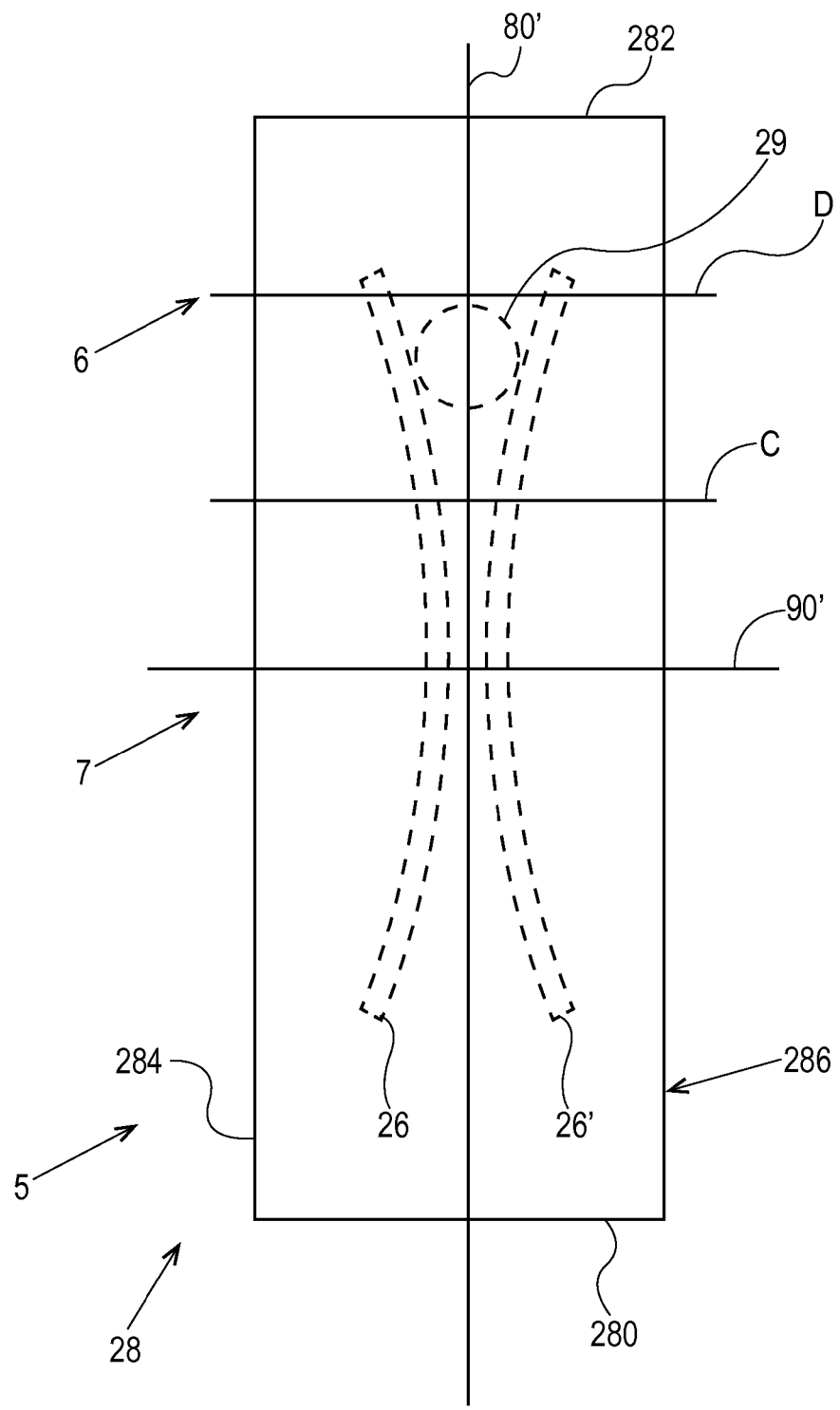
FIG. 12 is a top view of an absorbent core for an absorbent article in accordance with a non-limiting embodiment of the present disclosure.
Figure 13:
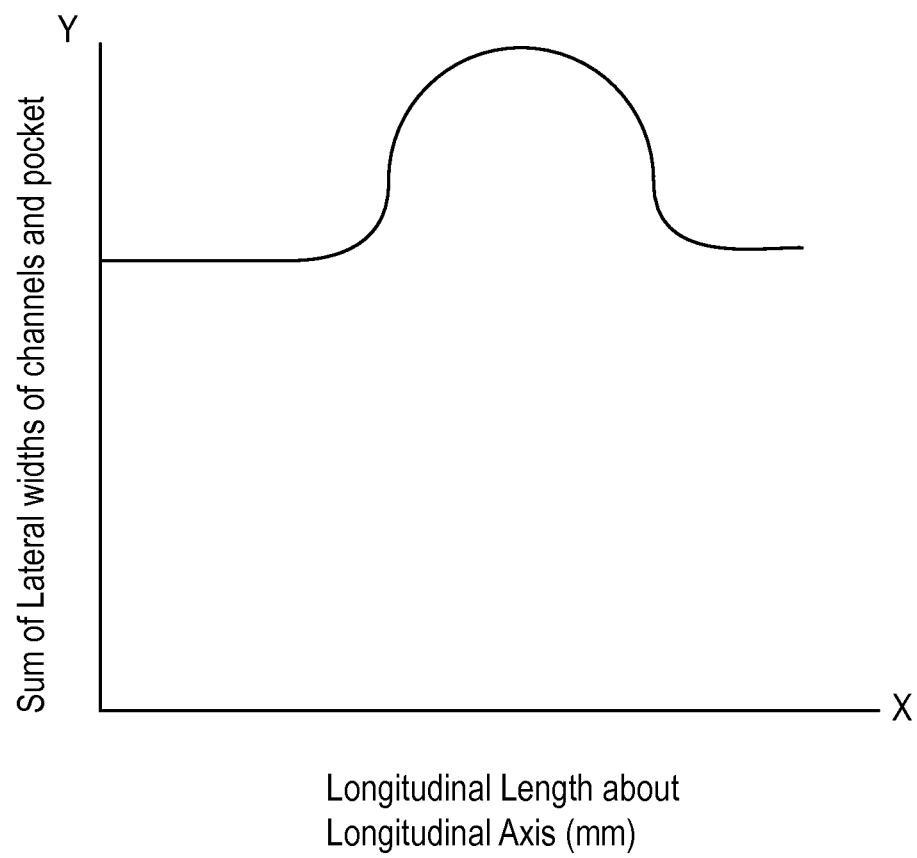
FIG. 13 is a profile of the sum of the lateral widths of portions of the channels and the pocket of FIG. 12 graphed against the longitudinal length of the channels between lines C and D of FIG. 12 in accordance with a non-limiting embodiment of the present disclosure.
Figure 14:
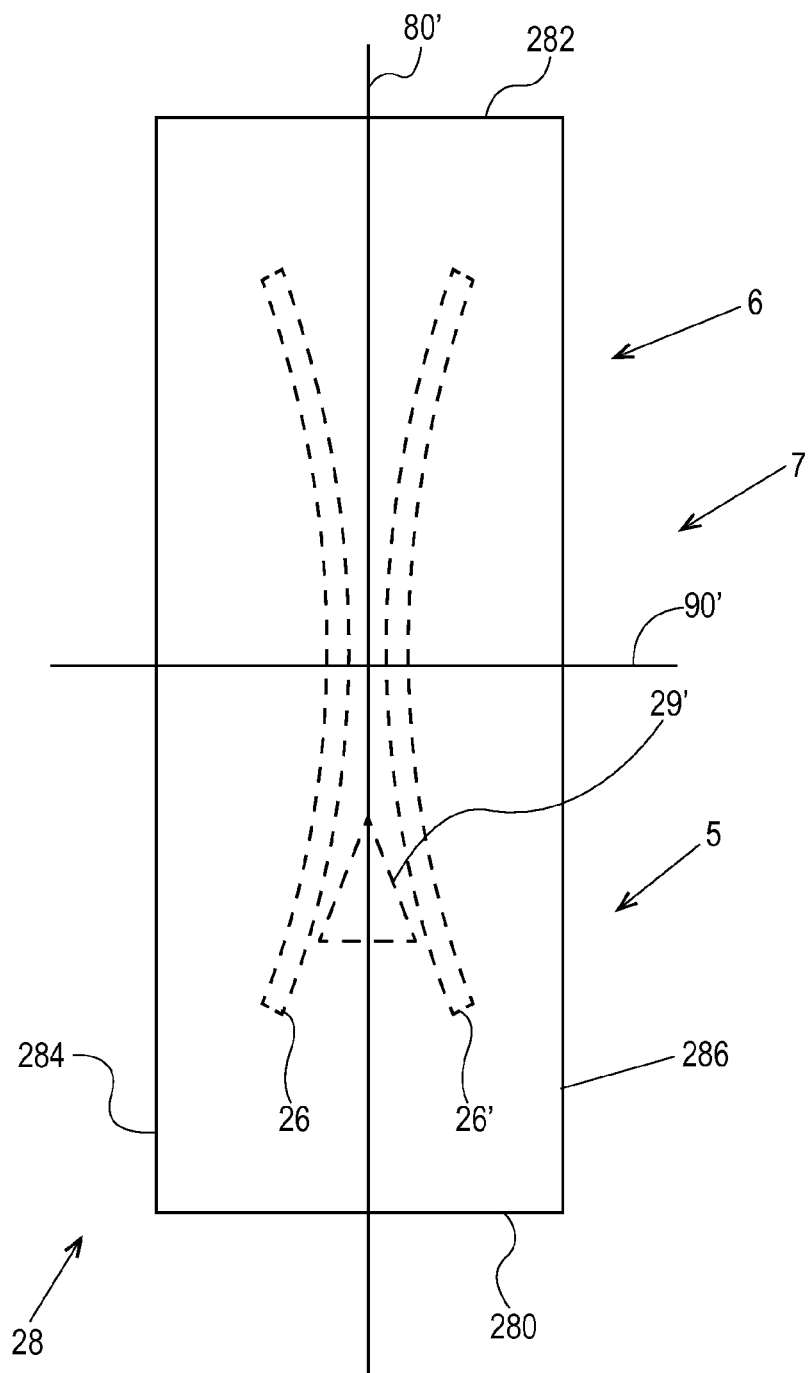
FIGS. 14-21 are top views of absorbent cores for absorbent articles in accordance with various non-limiting embodiments of the present disclosure.
Figure 15:
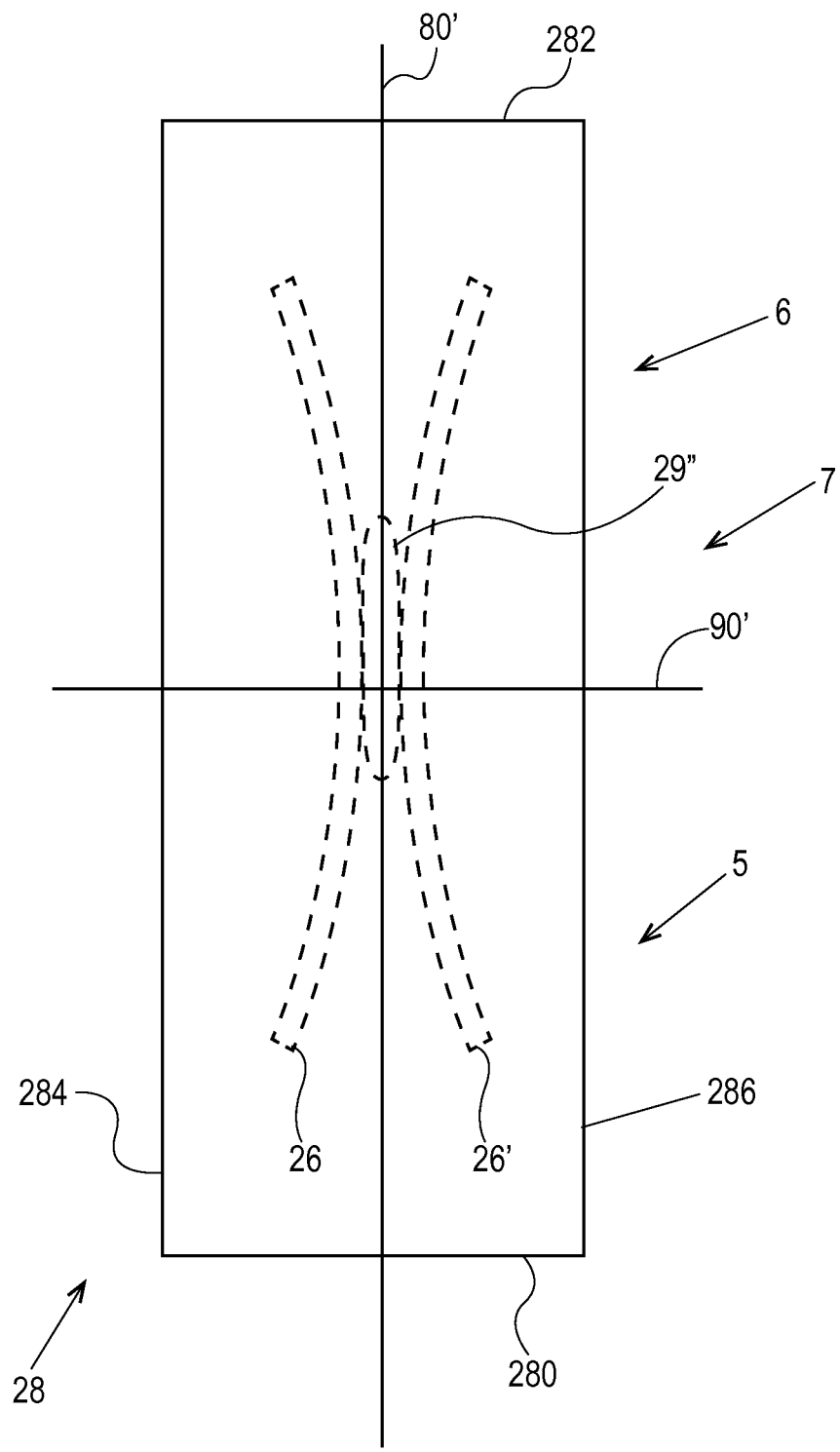

In another embodiment, referring to FIG. 12, the absorbent core 28 may comprise the first channel 26 and the second channel 26' as described above and one or more pockets 29 that are free of, or substantially free of, the superabsorbent polymers. As an example, the pocket 29 may have a width dimension of 20 mm to 110 mm or less or greater, such as 90 mm (about the lateral axis 90') and a length dimension of 30 mm to 00 mm or less or greater, such as 50 mm (about the longitudinal axis 80'). The one or more pockets 29 may have a portion positioned on the longitudinal axis 80' and may be positioned in the front waist region 5, the rear waist region 6, and/or the crotch region 7. In another embodiment, a pocket may extend into two or more regions. Although FIGS. 9, 12 and 14-20 only show an absorbent core 28, it will be understood that the front waist region 5, the rear waist region 6, and the crotch region 7 will generally correspond with such regions on the absorbent article as illustrated in FIG. 1. A portion of the one or more pockets 29 may not be positioned on the longitudinal axis 80'. In an embodiment, the one or more pockets 29 may have a portion positioned on the lateral axis 90'. The pocket 29 has lateral widths measured parallel to the lateral axis 90' and longitudinal lengths measured parallel to the longitudinal axis 80'. A profile of the sum of the lateral widths of the first and second channels 26 and 26' and the lateral widths of the pocket 29 over a longitudinal length of 50 mm taken along the longitudinal axis 80' may have two separate, constant, or substantially constant portions, as illustrated in representative form in FIG. 13. FIG. 13 is the sum of the lateral widths of the superabsorbent polymer free, or substantially superabsorbent polymer free, areas of the channels 26 and 26' and the pocket 29 taken from line C to line D in FIG. 12. The longitudinal length along the longitudinal axis 80' between lines C and D may be at least 50 mm or less or more. As can be seen from FIG. 13, the profile has two constant, or substantially constant portions, representing the sum of the lateral widths of the channels alone, and one portion larger than the constant, or substantially constant portions, representing the sum of the lateral widths of the channels 26 and 26' and the lateral widths of the pocket 29. The sum of the lateral widths of the first channel 26, the second channel 26', and the pocket 29 at a point intermediate lines C and D may be in the range of about 20 mm to about 100 mm, for example. The lateral widths should be measured every 5 mm along the longitudinal axis 80' as discussed above and between lines C and D. The pocket 29 may be a bowel movement "BM" pocket configured to retain BM. In another embodiment, referring to FIG. 14, the pocket 29' may be positioned at least partially in the front waist region 5 and may be a urine management or retention pocket. In still another embodiment, referring to FIG. 15, the pocket 29" may be positioned at least partially in the crotch region 7 and may be a urine management or retention pocket and/or a BM pocket. The pocket 29" may have longitudinal side edges formed by the laterally inboard sides of the channels 26 and 26' or may have longitudinal side edges formed independently of the laterally inboard side edges of the channels 26 and 26'. The pockets 29, 29', or 29" may have lateral widths measured parallel to the lateral axis 90' every 5 mm along the longitudinal axis 80' in the range of 10 mm to 110 mm, 20 mm to 100 mm, or 30 mm to 95 mm, specifically reciting all 1 mm increments within the above-specified ranges and any ranges formed therein or thereby.

Figure 16:
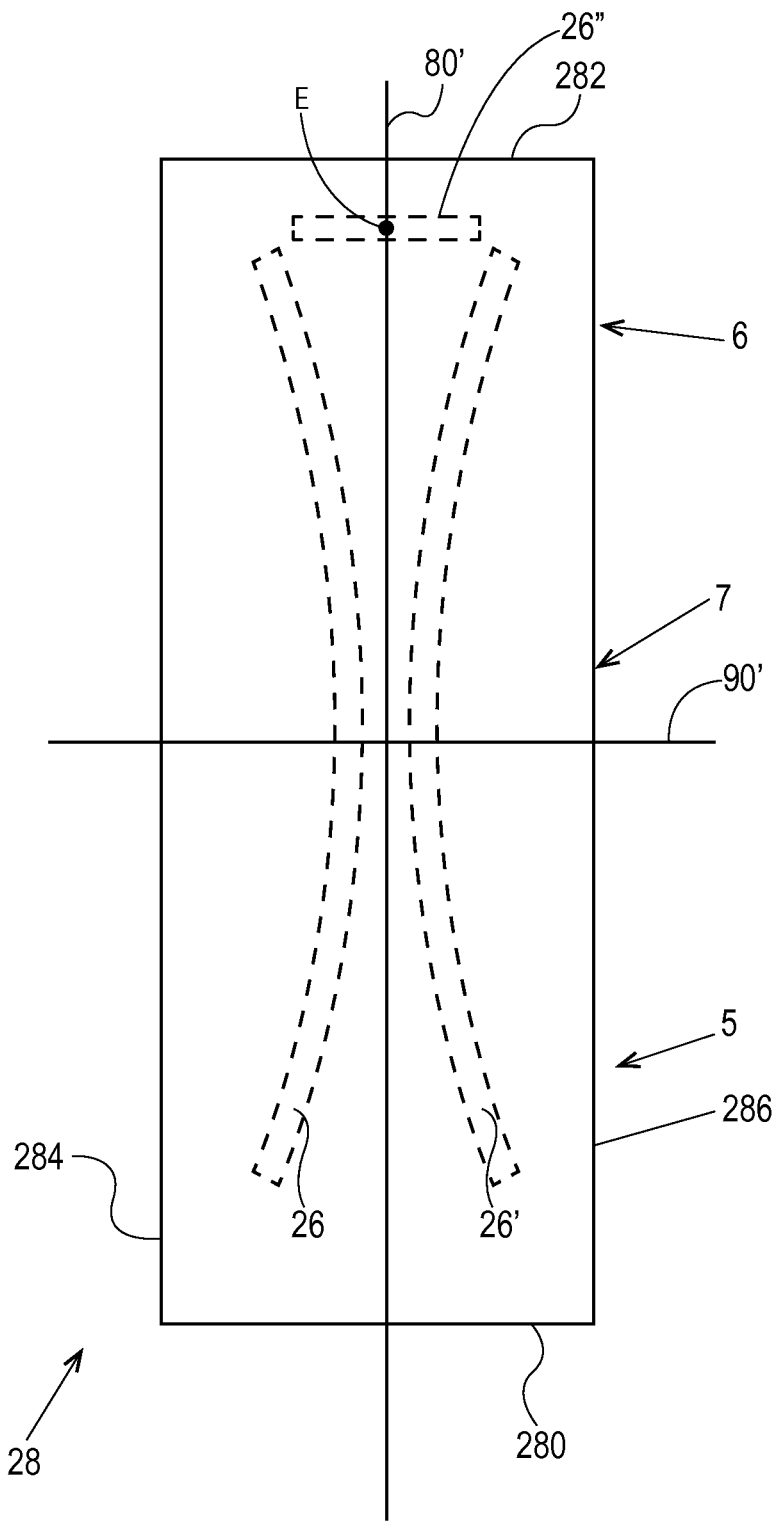
Figure 17:
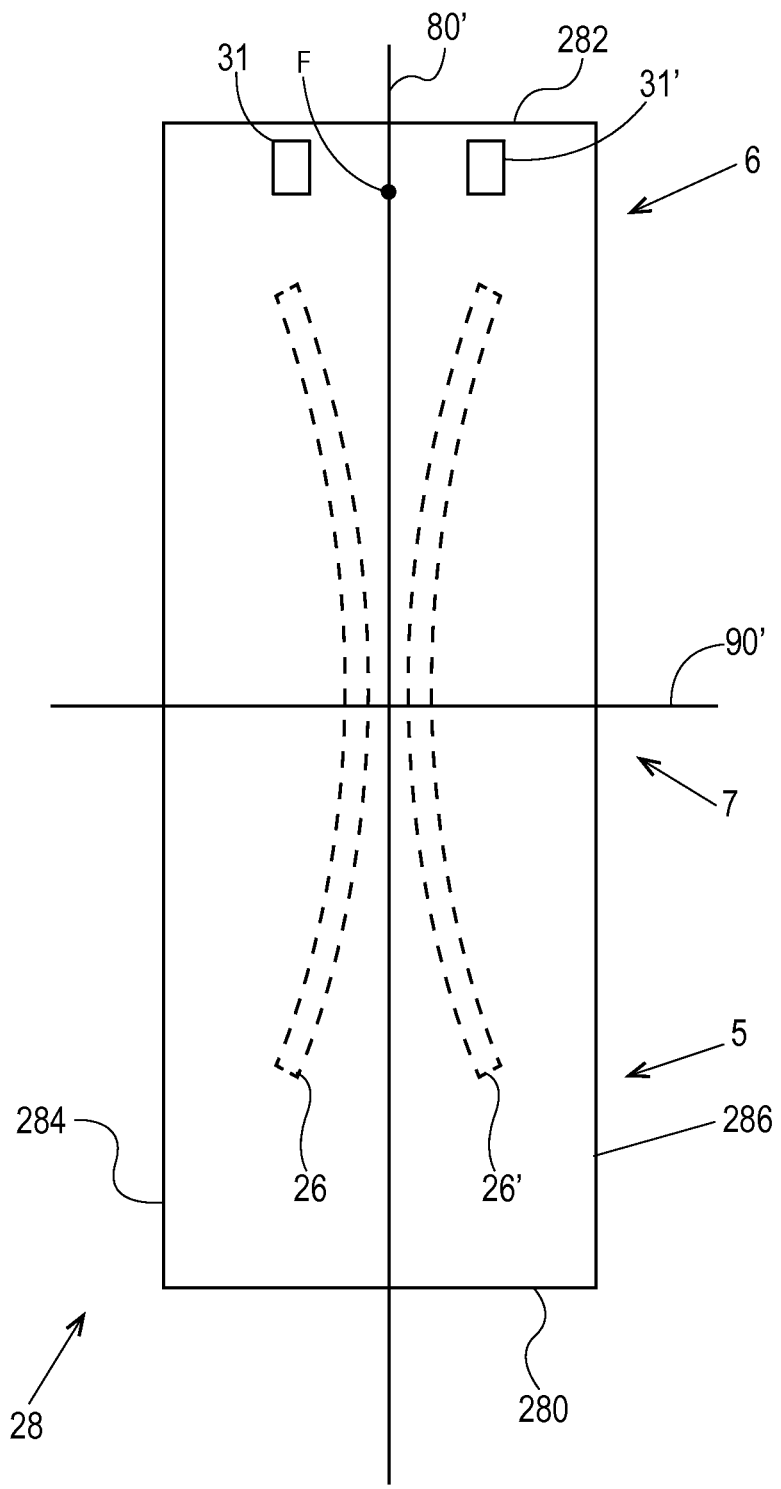

In yet another embodiment, referring to FIG. 16, the absorbent core 28 may comprise the first channel 26 and/or the second channel 26' and a third channel 26" (sometimes referred to in the claims as a second channel if one of the first and second channels 26 and 26' are not recited). The third channel 26" may be free of, or substantially free of, superabsorbent polymers and may be positioned in the rear waist region 6, the crotch region 7, and/or the front waist region 5. The third channel 26" may be positioned within 0-50 mm from the rear waist edge 12 or the rear side 282 or within 0-50 mm from the front waist edge 10 or the front side 280. All 1 mm increments within the above-specified ranges are specifically recited herein including any ranges formed therein or thereby. A sum of the lateral widths of the first channel 26 and the third channel 26" or the first channel 26, the second channel 26', and the third channel 26" at a point along the longitudinal axis (for example, point E of FIG. 16) that is 50 mm, or 30 mm, or 20 mm, or 15 mm, or 10 mm, or 5 mm, or 1 mm, or less from the rear side 282 or the rear waist edge 12 or the front side 280 or front waist edge 10 may be greater than zero. FIG. 17 illustrates an absorbent core 28 comprising a first channel 26, a second channel 26', a third channel 31, and a fourth channel 31'. Any of these channels may be optional. The sum of the lateral widths of the third channel 31 and the fourth channel 31' at a point along the longitudinal axis 80' (for example, point F of FIG. 17) that is 50 mm, or 30 mm, or 20 mm, or 15 mm, or 10 mm, or 5 mm, or 3 mm, or 1 mm, or less from the rear waist edge 12, the rear side 282, the front waist edge 10, or the front side 280 may be greater than zero.

Figure 18:
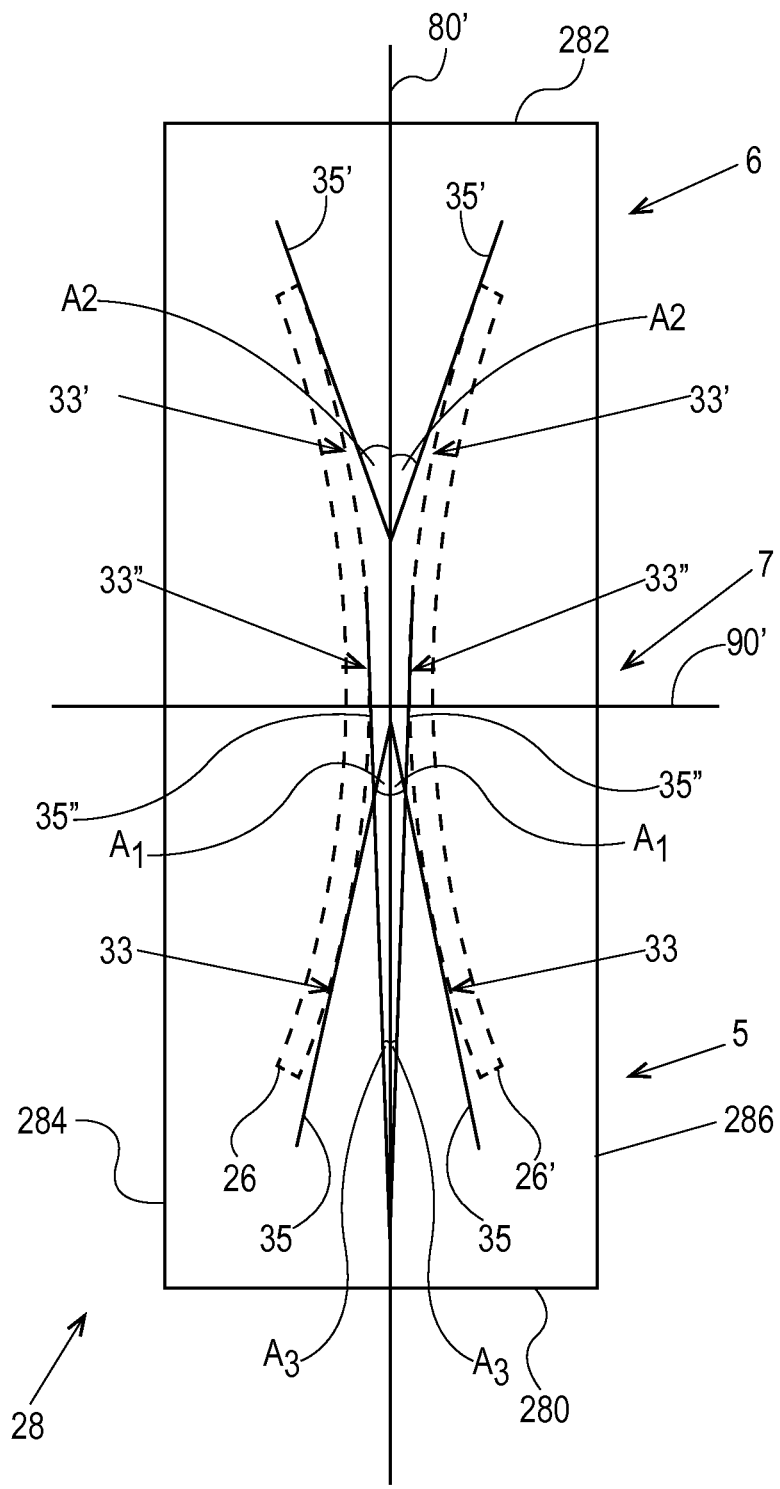

In an embodiment, referring to FIG. 18, the first channel 26 and the second channel 26' may each have a first arcuate portion 33 in the front waist region 5 and a second arcuate portion 33' in the rear waist region 6. The arcuate portions 33 and 33' may face the longitudinal axis 80'. The first channel 26 and the second channel 26' may also have a third arcuate portion 33" in the crotch region 7 or a non-arcuate portion in 33" the crotch region 7. The arcuate portions 33" or the portions 33" may also face the longitudinal axis 80'. Tangent lines 35 of the arcuate portions 33 may intersect the longitudinal axis 80' to create angle A1. The angle of intersection A1 between the tangent lines 35 and the longitudinal axis 80' may be in the range of 10 degrees to 80 degrees, 20 degrees to 75 degrees, 30 degrees to 60 degrees, or 45 degrees. Tangent lines 35' of the arcuate portions 33' may intersect the longitudinal axis 80' to create angle A2. The angle of intersection A2 between the tangent lines 35' and the longitudinal axis 80' may be in the range of 10 degrees to 80 degrees, 20 degrees to 75 degrees, 30 degrees to 60 degrees, or 45 degrees. Tangent lines 35" of the arcuate portions 33" may intersect the longitudinal axis 80' to create angle A3. The angle of intersection A3 between the tangent lines 35" and the longitudinal axis 80' may be in the range of 0.1 degrees to 35 degrees or 1 degree to 20 degrees. In an embodiment, tangent lines may extend from the non-arcuate portions 33" in the crotch region 7. The tangent lines may not intersect the longitudinal axis 80' and may instead extend in directions parallel to the longitudinal axis 80'. All 0.5 degree increments within the ranges specified in this paragraph are recited herein including any ranges formed therein or thereby.

As can be seen in FIG. 18, the first tangent line 35 taken from the first arcuate portion 33 on a first side of the longitudinal axis 80' may have a positive slope (rise/run) and the first tangent line 35 taken from the first arcuate portion 33 on the second side of the longitudinal axis 80' may have a negative slope. The second tangent line 35' taken from the second arcuate portion 33' on a first side of the longitudinal axis 80' may have a negative slope and the second tangent line 35' taken from the second arcuate portion 33' on the second side of the longitudinal axis 80' may have a positive slope. The tangent lines 35" may also have a positive or a negative slope. The slopes of the various tangent lines may be different if the configuration of the channels is different.

Again referring to FIG. 18, angles A1, A2, and A3 on a first side of the longitudinal axis 80' may be different than, the same as, or substantially the same as angles A1, A2, and A3, respectively, on a second side of the longitudinal axis 80'. In an embodiment, with respect to angles on one side of the longitudinal axis 80', angle A1 may be greater than angles A2 and A3 and angle A2 may be greater than angle A3. In other embodiments, with respect to angles on one side of the longitudinal axis 80', angle A1 and angle A2 may be the same or substantially the same, while angle A3 may be less than angles A1 and A2. In still other embodiments, any of the angles on one side of the longitudinal axis 80' may be the same or different.

The tangent lines 35 are taken from portions of the arcuate portions 33 in the front waist region 5. The tangent lines 35' are taken from portions of the arcuate portions 33' in the rear waist region 6. The tangent lines 35" are taken from portions of the arcuate portions 33" in the crotch region 7.

The longitudinal axis 80 or 80' can be drawn on an absorbent article or the absorbent core, respectively, by connecting the midpoints of the first waist edge 10 or first side 280 and the second waist edge 12 or second side 282, respectively. The tangent lines can be drawn on the absorbent article or the absorbent core using a straight edge. Multiple tangent lines may be drawn on an arcuate portion in the front waist region 5, the rear waist region 6, and/or the crotch region 7. The tangent lines should be drawn long enough to intersect the longitudinal axis 80 or 80' unless they are positioned parallel to the longitudinal axis 80 or 80'. A protractor, graduated in 1 degree increments, may then be used to measure the angles (A1, A2, and A3) between the tangent lines and the longitudinal axis 80 or 80'. If additional channels are present in the absorbent core 28, additional tangent lines may be drawn on those channels in the same or a similar fashion.

Figure 19:
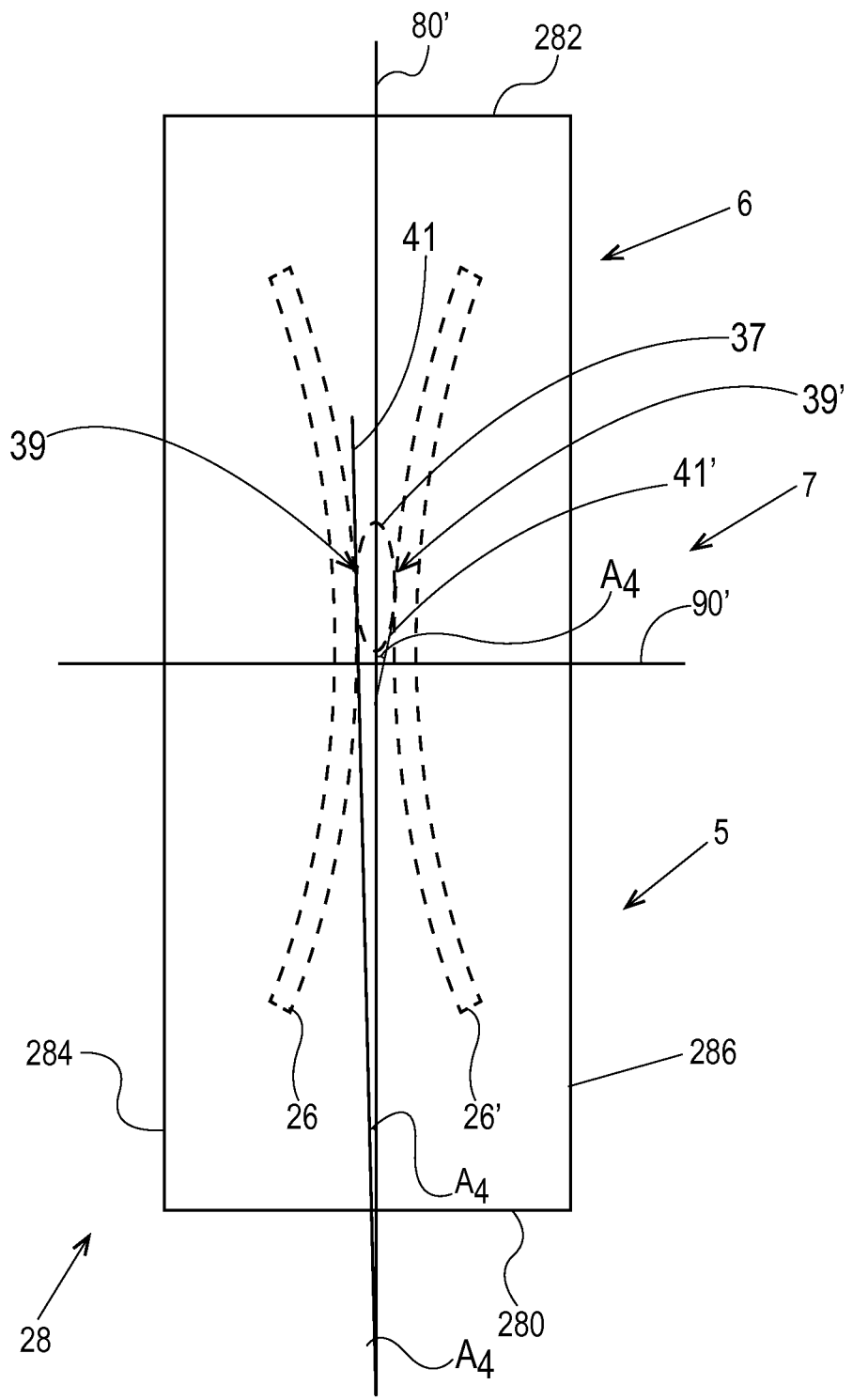

In an embodiment, referring to FIG. 19, in additional to the first and second channels 26 and 26' discussed above, an absorbent core may comprise a channel or pocket 37 that is free of, or substantially free of, superabsorbent polymers. A portion of the channel or pocket 37 may be located on the longitudinal axis 80'. The channel or pocket 37 may comprise an arcuate portion 39 facing the side 284 or the second side edge 4 and another arcuate portion 39' facing the side 282 or the first side edge 3. An angle, A4, between a tangent line 41' (or 41) of the arcuate portion 39' (or 39) and the longitudinal axis 80' may be in the range of about 0.1 degrees to 40 degrees, 0.1 degrees to 20 degrees, 0.1 degrees to 15 degrees, 0.1 degrees to 10 degrees, or 0.1 degrees to five degrees, specifically reciting all 0.1 degree increments within the above-specified ranges and any ranges formed therein or thereby. In an embodiment, the tangent line 41 (or 41') may extend parallel to the longitudinal axis 80' and never intersect the longitudinal axis 80'. The channel or pocket 37 may be positioned at least partially within the front waist region 5, the rear waist region 6, and/or the crotch region 7.

Figure 20:
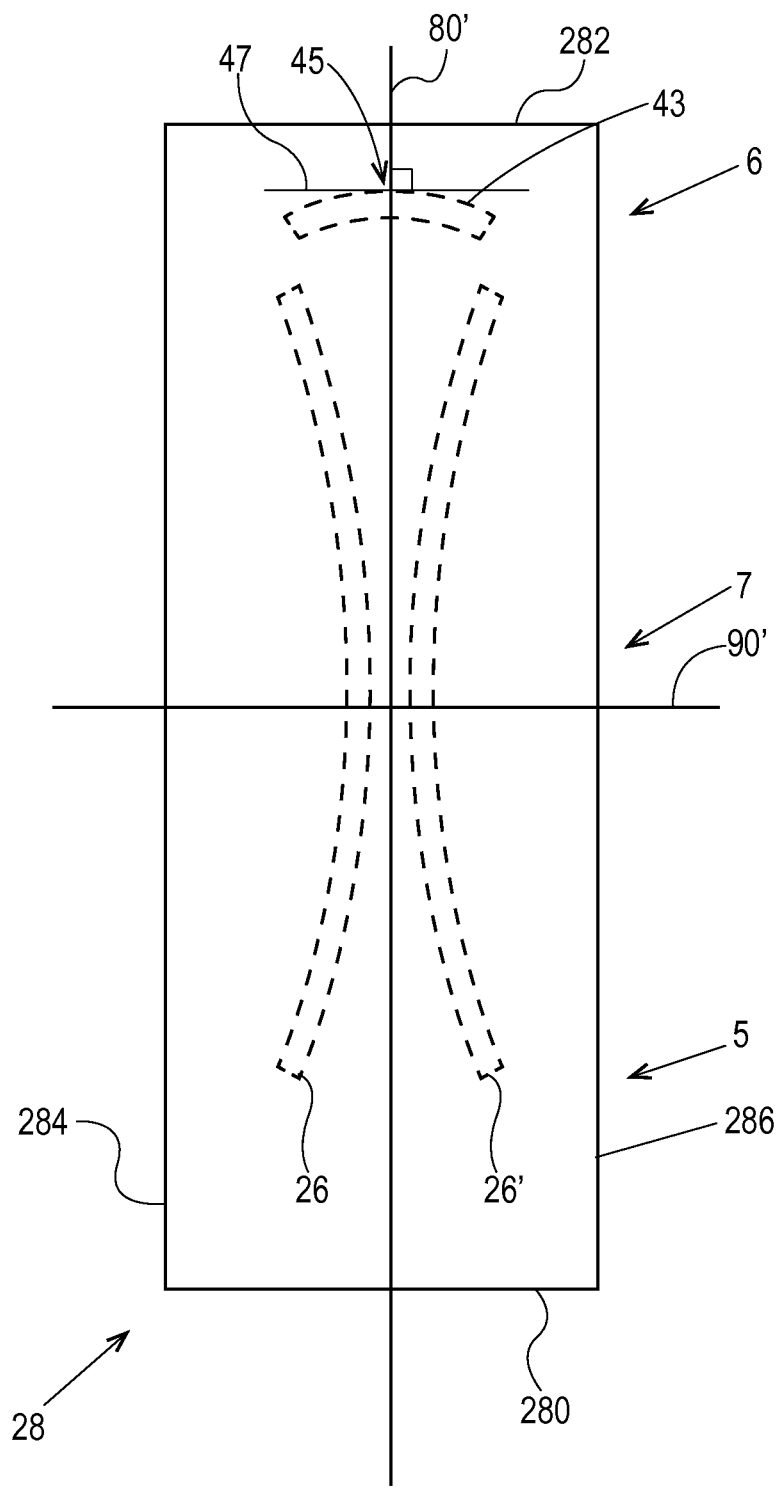

In an embodiment, referring to FIG. 20, in addition to the first and second channels 26 and 26', an absorbent core 28 may comprise a channel or a pocket 43 having a portion positioned on the longitudinal axis 80'. The channel or pocket 43 may have a longitudinal length in the range of 10 mm to 150 mm and a lateral width of 10 mm to about 150 mm, specifically reciting all 1 mm increments within the specified ranges and all ranges formed therein or thereby. Other dimensions are also within the scope of the present disclosure. The channel or the pocket 43 may be located in the front waist region 5 or the rear waist region 6, or both. The channel or pocket 43 may have an arcuate portion 45 facing the front side 280 or the front waist edge 10 if the channel or pocket 43 is located in the front waist region 5 and an arcuate portion 45 facing the rear side 282 or the rear waist region 12 if the channel or pocket 43 is located in the rear waist region 6. The channel or pocket 43 may extend into the crotch region 7 in some instances. A tangent line 47 of the arcuate portion 45 may create an angle with the longitudinal axis 80' in the range of 70 degrees to 110 degrees, 80 degrees to 100 degrees, 85 degrees to 85 degrees, about 90 degrees, or 90 degrees, specifically reciting all 0.5 degree increments within the specified ranges and any ranges formed therein or thereby.

Figure 21:
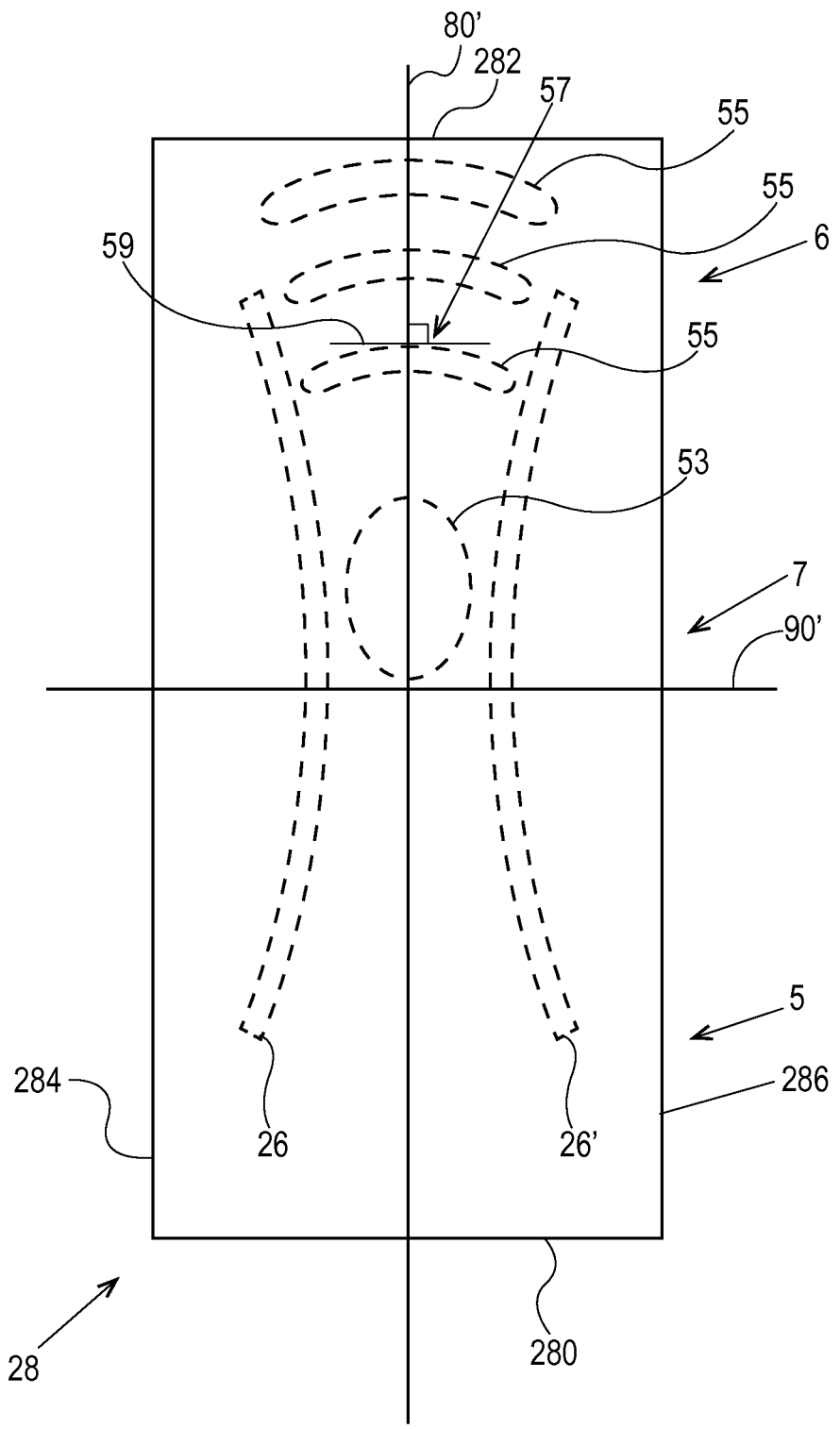

In an embodiment, referring to FIG. 21, in addition to the first and second channels 26 and 26', an absorbent core 28 may comprise a pocket 53 in the crotch region 7 and/or the rear waist region 6 and one or more channels 55 in the rear waist region 6 and/or the crotch region 7. In another embodiment, the pocket 53 may be in the crotch region 7 and/or the front waist region 5 and the one or more channels 55 may be in the crotch region 7 and/or the front waist region 5. The pocket 53 and the one or more channels 55 may be BM pockets or channels and/or urine management pockets and/or channels. The channels 55 may extend generally in the lateral direction about the lateral axis 90'. The various parameters discussed herein may apply to FIG. 21, if suitable. For instance, at least one, or all of, the channels 55 may have a tangent line 59 extending from an arcuate portion 57 thereof. The angle formed between the tangent line 59 and the longitudinal axis 80' may be 80 degrees to 100 degrees, about 90 degrees, or 90 degrees, for example.

Barrier Leg Cuffs

The absorbent article may comprise a pair of barrier leg cuffs 34. Each barrier leg cuff may be formed by a piece of material which is bonded to the article so it can extend upwards from the inner surface of the article and provide improved containment of liquids and other body exudates approximately at the junction of the torso and legs of the wearer. The barrier leg cuffs are delimited by a proximal edge 64 joined directly or indirectly to the topsheet 24 and/or the backsheet 25 and a free terminal edge 66, which is intended to contact and form a seal with the wearer's skin. The barrier leg cuffs extend at least partially between the front waist edge 10 and the rear waist edge 12 of the absorbent article on opposite sides of the longitudinal axis 80 and are at least present at the level of the crotch point (C) or crotch region. The barrier leg cuffs may be joined at the proximal edge 64 with the chassis of the article by a bond 65 which may be made by gluing, fusion bonding, or combination of other suitable bonding processes. The bond 65 at the proximal edge 64 may be continuous or intermittent. The bond 65 closest to the raised section of the leg cuffs delimits the proximal edge 64 of the standing up section of the leg cuffs.

The barrier leg cuffs may be integral with the topsheet 24 or the backsheet 25 or may be a separate material joined to the article's chassis. The material of the barrier leg cuffs may extend through the whole length of the diapers but may be "tack bonded" to the topsheet 24 towards the front waist edge 10 and rear waist edge 12 of the article so that in these sections the barrier leg cuff material remains flush with the topsheet 24.

Each barrier leg cuff 34 may comprise one, two or more elastic strings 35 close to this free terminal edge 66 to provide a better seal.

In addition to the barrier leg cuffs 34, the article may comprise gasketing cuffs 32, which are joined to the chassis of the absorbent article, in particular to the topsheet 24 and/or the backsheet 25 and are placed externally relative to the barrier leg cuffs. The gasketing cuffs 32 may provide a better seal around the thighs of the wearer. Each gasketing leg cuff may comprise one or more elastic strings or elastic elements in the chassis of the absorbent article between the topsheet 24 and backsheet 25 in the area of the leg openings.

U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describes disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

Acquisition-Distribution System

The absorbent articles of the present disclosure may comprise an acquisition-distribution layer or system 50 (herein "ADS"). One function of the ADS is to quickly acquire the fluid and distribute it to the absorbent core in an efficient manner. The ADS may comprise one, two or more layers, which may form a unitary layer or may remain as discrete layers which may be attached to each other. In an embodiment, the ADS may comprise two layers: a distribution layer 54 and an acquisition layer 52 disposed between the absorbent core and the topsheet, but the present disclosure is not limited to this embodiment.

The ADS may comprise SAP as this may slow the acquisition and distribution of the fluid. Suitable ADS are described in WO 2000/59430 (Daley), WO 95/10996 (Richards), U.S. Pat. No. 5,700,254 (McDowall), and WO 02/067809 (Graef), for example.

Distribution Layer

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under baby weight. This provides the core with a higher void volume, permeability, and liquid absorption, and hence reduced leakage and improved dryness.

Example chemically cross-linked cellulosic fibers suitable for a distribution layer are disclosed in U.S. Pat. Nos. 5,549,791, 5,137,537, WO 9534329, or U.S. Pat. Publ. No. 2007/118087. Example cross-linking agents include polycarboxylic acids such as citric acid and/or polyacrylic acids such as acrylic acid and maleic acid copolymers.

The distribution layer comprising cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 54 may be a material having a water retention value of from 25 to 60 or from 30 to 45, measured as indicated in the procedure disclosed in U.S. Pat. No. 5,137,537.

The distribution layer may typically have an average basis weight of from 30 to 400 $g/m^2$ or from 100 to 300 $g/m^2$, specifically reciting all 1.0 $g/m^2$ increments within the above-specified ranges and any ranges formed therein or thereby. The density of the distribution layer may vary depending on the compression of the article, but may be between 0.03 to 0.15 $g/cm^3$ or 0.08 to 0.10 $g/cm^3$, specifically reciting all 1.0 $g/cm^3$ increments within the above-specified ranges and any ranges formed therein or thereby, measured at 0.30 psi (2.07 kPa).

Acquisition Layer

The ADS may comprise an acquisition layer 52. The acquisition layer may be disposed between the distribution layer 54 and the topsheet 24. The acquisition layer 52 may be or may comprise a non-woven material, such as an SMS or SMMS material, comprising a spunbonded, a melt-blown and a further spunbonded layer or alternatively a carded chemical-bonded nonwoven. The nonwoven material may be latex bonded. Example upper acquisition layers 52 are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An example binder is a butadiene/styrene latex. Nonwovens have the advantage that they can be manufactured outside the converting line and stored and used as a roll of material.

The acquisition layer 52 may be stabilized by a latex binder, for example a styrene-butadiene latex binder (SB latex).

A further acquisition layer may be used in addition to a first acquisition layer described above. For example, a tissue layer may be placed between the first acquisition layer and the distribution layer. The tissue may have enhanced capillarity distribution properties compared to the acquisition layer described above. The tissue and the first acquisition layer may be of the same size or may be of a different size. For example, the tissue layer may extend further in the rear of the absorbent article than the first acquisition layer. An example of hydrophilic tissue is a 13-15 gsm high wet strength made of cellulose fibers from supplier Havix.

Fastening System

The absorbent article may include a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 44 is normally provided on the garment-facing surface of the front waist region 5 for the fastener to be releasably attached thereto. Some example surface fastening systems are disclosed in U.S. Pat. Nos. 3,848,594, 4,662,875, 4,846,815, 4,894,060, 4,946,527, 5,151,092, and 5,221,274. An example interlocking fastening system is disclosed in U.S. Pat. No. 6,432,098. The fastening system may also provide a mechanism for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Front and Rear Ears

In an embodiment, the absorbent article may comprise front ears 46 and rear ears 40. The ears may be an integral part of the chassis, such as formed from the topsheet 24 and/or backsheet 26 as side panel. Alternatively, as represented on FIG. 1, the ears may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the absorbent article. Disposable diapers may be constructed so as to have two elastic waist features, one positioned in the front waist region and one positioned in the rear waist region. The elastic waist feature may be constructed in a number of different configurations including those described in U.S. Pat. Nos. 4,515,595, 4,710,189, 5,151,092, and 5,221,274.

Relations Between the Layers

Typically, adjacent layers and components may be joined together using conventional bonding methods, such as adhesive coating via slot coating or spraying on the whole or part of the surface of the layer, thermo-bonding, pressure bonding, or combinations thereof. This bonding is not represented in the Figures (except for the bonding between the raised element of the leg cuffs 65 with the topsheet 24) for clarity and readability, but bonding between the layers of the article should be considered to be present unless specifically excluded. Adhesives may be used to improve the adhesion of the different layers between the backsheet 25 and the core wrap. The glue may be any suitable hotmelt glue known in the art.

If an acquisition layer 52 is present, it may be desired that this acquisition layer is larger than or least as large as the distribution layer 54 in the longitudinal and/or transversal dimension. Thus, the distribution layer 52 may be deposited on the acquisition layer. This simplifies handling, in particular if the acquisition layer is a nonwoven which may be unrolled from a roll of stock material. The distribution layer may also be deposited directly on the absorbent core's upper side of the core wrap or another layer of the article. Also, having an acquisition layer 52 that is larger than the distribution layer allows for direct gluing of the acquisition layer to the storage core (at the larger areas). This may provide increased patch integrity and better liquid communication.

The absorbent core and in particular its absorbent material deposition area 8 may be at least as large and long and at least partially larger and/or longer than the acquisition-distribution system (ADS). This is because the absorbent material in the core may more effectively retain fluid and provide dryness benefits across a larger area than the ADS. The absorbent article may have a rectangular SAP layer and a non-rectangular (shaped) ADS. The absorbent article may also have a rectangular (non-shaped) ADS and a rectangular layer of SAP.

Sanitary Napkin Features

Figure 22:
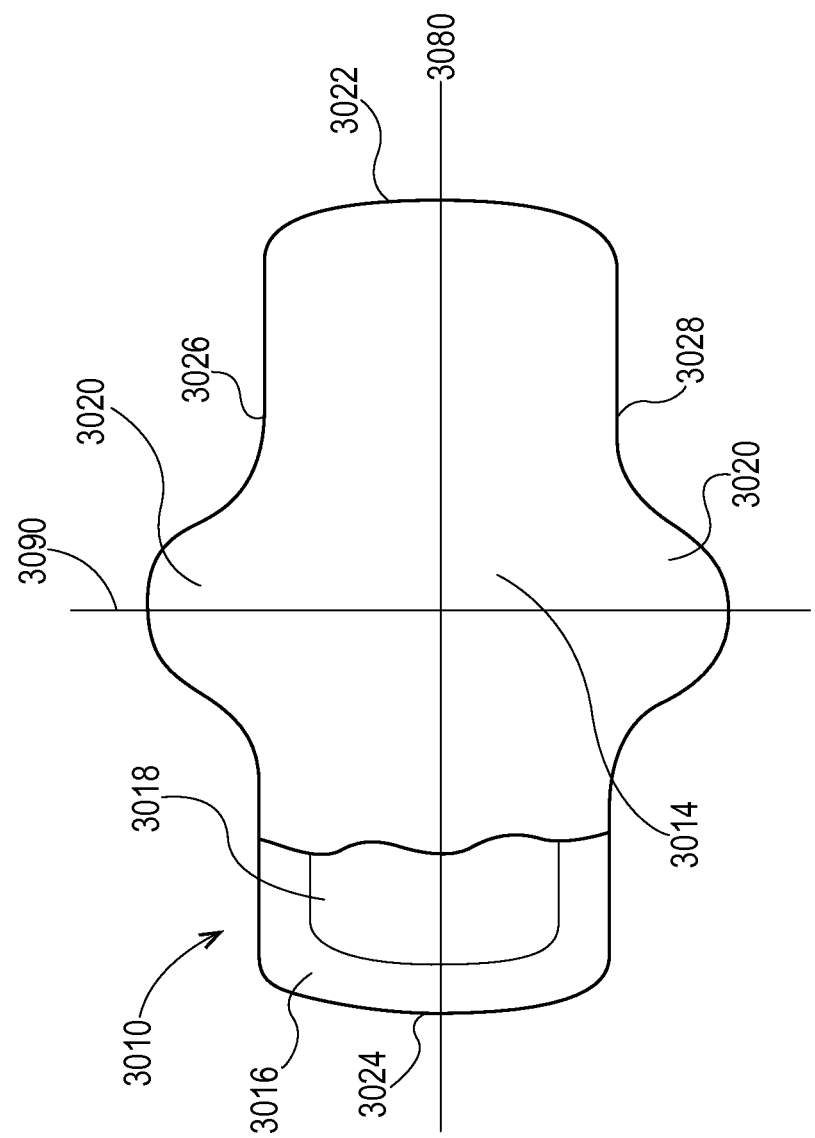
FIG. 22 is a top view of an absorbent article that is a sanitary napkin with some of the layers cut away in accordance with a non-limiting embodiment of the present disclosure.

In an embodiment, referring to FIG. 22, the absorbent article may be a sanitary napkin 3010. The sanitary napkin 3010 may comprise a liquid permeable topsheet 3014, a liquid impermeable, or substantially liquid impermeable, backsheet 3016, and an absorbent core 3018. The absorbent core 3018 may have any or all of the features described herein with respect to the absorbent cores 28 and, in some embodiments, may have a secondary topsheet instead of the acquisition-distribution system disclosed above. The sanitary napkin 3010 may also comprise wings 3020 extending outwardly with respect to a longitudinal axis 3080 of the sanitary napkin 3010. The sanitary napkin 3010 may also comprise a lateral axis 3090. The wings 3020 may be joined to the topsheet 3014, the backsheet 3016, and/or the absorbent core 3018. The sanitary napkin 3010 may also comprise a front edge 3022, a rear edge 3024 longitudinally opposing the front edge 3022, a first side edge 3026, and a second side edge 3028 longitudinally opposing the first side edge 3026. The longitudinal axis 3080 may extend from a midpoint of the front edge 3022 to a midpoint of the rear edge 3024. The lateral axis 3090 may extend from a midpoint of the first side edge 3028 to a midpoint of the second side edge 3028. The sanitary napkin 3010 may also be provided with additional features commonly found in sanitary napkins as is known in the art.

Method of Making the Article

The absorbent articles and sanitary napkins of the present disclosure may be made by any suitable methods known in the art. In particular, the articles may be hand-made or industrially produced at high speed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. An absorbent article comprising:
   a front waist edge;
   a rear waist edge longitudinally opposing the front waist edge;
   a longitudinal axis extending from a midpoint of the front waist edge to a midpoint of the rear waist edge;
   a liquid permeable topsheet;
   a liquid impermeable backsheet;
   a pair of barrier leg cuffs extending at least partially between the front waist edge and the rear waist edge on opposite sides of the longitudinal axis, wherein each barrier leg cuff comprises:
      a proximal edge joined to the topsheet or the backsheet; and
      a free terminal edge; and
   an absorbent core disposed at least partially intermediate the topsheet and the backsheet and comprising a core wrap enclosing an absorbent material, wherein the core wrap comprises a first material and a second material, wherein the first material forms a C-wrap only partially around the second material, wherein the absorbent material comprises at least 80% of superabsorbent polymers by weight of the absorbent material, wherein the absorbent core comprises a continuous channel substantially free of the superabsorbent polymers and at least partially oriented in the longitudinal direction of the article, wherein the channel has an arcuate portion facing the longitudinal axis, and wherein an angle between a tangent line of the arcuate portion and the longitudinal axis is greater than or equal to 20 degrees.

2. The absorbent article of claim 1, wherein the angle is greater than or equal to 30 degrees.

3. The absorbent article of claim 1, wherein the angle is greater than or equal to 45 degrees.

4. The absorbent article of claim 1, wherein the angle is greater than or equal to 60 degrees.

5. The absorbent article of claim 1, wherein the angle is greater than or equal to 75 degrees.

6. The absorbent article of claim 1, wherein the absorbent core comprises a second continuous channel substantially free of the superabsorbent polymers and at least partially oriented in the longitudinal direction of the article, wherein the second channel is positioned on an opposite side of the longitudinal axis as the channel, wherein the second channel has a second arcuate portion facing the longitudinal axis, wherein a second angle between a second tangent line taken from the second arcuate portion and the longitudinal axis is greater than or equal to 20 degrees, and wherein the second tangent line has a positive or a negative slope.

7. The absorbent article of claim 6, wherein the channel is symmetrical to the second channel about the longitudinal axis.

8. The absorbent article of claim 1, comprising a front waist region and a rear waist region separated by a lateral axis extending perpendicular to a midpoint of the longitudinal axis, wherein the arcuate portion is in the front waist region, and wherein the first tangent line has a positive slope.

9. The absorbent article of claim 8, wherein the channel comprises a second arcuate portion facing the longitudinal axis in the rear waist region, wherein a second angle between a second tangent line of the second arcuate portion and the longitudinal axis is different than the angle, and wherein the second tangent line has a negative slope.

10. The absorbent article of claim 9, wherein the second angle is greater than the angle.

11. The absorbent article of claim 9, wherein the second angle is less than the angle.

12. The absorbent article of claim 1, comprising a front waist region, a rear waist region, and a crotch region positioned intermediate the front waist region and the rear waist region, wherein each of the three regions are ⅓ of the longitudinal length of the absorbent article, wherein the arcuate portion is in the front waist region, and wherein a second angle between a second tangent line of a portion of the channel in the crotch region and the longitudinal axis is less than the angle.

13. The absorbent article of claim 12, wherein the second angle is less than about 1 degree.

14. The absorbent article of claim 12, wherein the channel comprises a second arcuate portion facing the longitudinal axis in the rear waist region, and wherein a third angle between a third tangent line of the second arcuate portion and the longitudinal axis is different than the angle and the second angle.

15. The absorbent article of claim 14, wherein the third angle is smaller than the angle and larger than the second angle.

16. The absorbent article of claim 1, wherein the pair of barrier leg cuffs both extend outwardly from the topsheet.

17. An absorbent article comprising:
   a front waist edge;
   a rear waist edge longitudinally opposing the front waist edge;
   a longitudinal axis extending from a midpoint of the front waist edge to a midpoint of the rear waist edge;
   a liquid permeable topsheet;
   a liquid impermeable backsheet;
   a pair of barrier leg cuffs extending at least partially between the front waist edge and the rear waist edge on opposite sides of the longitudinal axis, wherein each barrier leg cuff comprises:
      a proximal edge joined to the topsheet or the backsheet; and
      a free terminal edge; and
   an absorbent core disposed at least partially intermediate the topsheet and the backsheet and comprising a core wrap enclosing an absorbent material, wherein the core wrap comprises a first material and a second material, wherein the first material forms a C-wrap only partially around the second material, wherein the absorbent material comprises at least 80% of superabsorbent polymers by weight of the absorbent material, wherein the absorbent core comprises a continuous channel or a continuous pocket substantially free of the superabsorbent polymers, wherein a portion of the channel or the pocket is located on the longitudinal axis, wherein the channel or the pocket has an arcuate portion facing the rear waist edge, and wherein an angle between a tangent line of the arcuate portion and the longitudinal axis is about 80-100 degrees.

18. The absorbent article of claim 17, wherein the angle between the tangent line of the arcuate portion and the longitudinal axis is about 90 degrees.

19. The absorbent article of claim 17, wherein the pair of barrier leg cuffs both extend upwardly relative to the topsheet.

20. An absorbent article comprising:
a front waist edge;
a rear waist edge longitudinally opposing the front waist edge;
a first side edge;
a second side edge laterally opposing the first side edge;
a longitudinal axis extending from a midpoint of the front waist edge to a midpoint of the rear waist edge;
a liquid permeable topsheet;
a liquid impermeable backsheet;
a pair of barrier leg cuffs extending at least partially between the front waist edge and the rear waist edge on opposite sides of the longitudinal axis, wherein each barrier leg cuff comprises:
    a proximal edge joined to the topsheet or the backsheet; and
    a free terminal edge; and
an absorbent core disposed at least partially intermediate the topsheet and the backsheet and comprising a core wrap enclosing an absorbent material, wherein the core wrap comprises a first material and a second material, wherein the first material forms a C-wrap only partially around the second material, wherein the absorbent material comprises at least 80% of superabsorbent polymers by weight of the absorbent material, wherein the absorbent core comprises a continuous channel or a continuous pocket substantially free of the superabsorbent polymers, wherein a portion of the channel or pocket is located on the longitudinal axis, wherein the channel or the pocket has an arcuate portion facing the first side edge, and wherein an angle between a tangent line of the arcuate portion and the longitudinal axis is about 0.1 degrees to about 10 degrees.

21. The absorbent article of claim 20, wherein the tangent line has a positive slope or a negative slope.

22. The absorbent article of claim 20, wherein the angle between the tangent line of the arcuate portion and the longitudinal axis is about 0.1 to about 5 degrees.

23. The absorbent article of claim 20, wherein the pair of barrier leg cuffs both extend upwardly relative to the topsheet.

24. A sanitary napkin comprising:
a front edge;
a rear edge longitudinally opposing the front edge;
a longitudinal axis extending from a midpoint of the front edge to a midpoint of the rear edge;
a liquid permeable topsheet;
a liquid impermeable backsheet; and
an absorbent core disposed at least partially intermediate the topsheet and the backsheet and comprising a core wrap enclosing an absorbent material, wherein the core wrap comprises a first material and a second material, wherein the first material forms a C-wrap only partially around the second material, wherein the absorbent material comprises at least 80% of superabsorbent polymers by weight of the absorbent material, wherein the absorbent core comprises a continuous channel substantially free of the superabsorbent polymers and at least partially oriented in the longitudinal direction of the article, wherein the channel has an arcuate portion facing the longitudinal axis, and wherein an angle between a tangent line of the arcuate portion and the longitudinal axis is greater than or equal to 20 degrees.

25. The absorbent article of claim 24, wherein the angle is greater than or equal to 45 degrees.

26. The absorbent article of claim 24, wherein the angle is greater than or equal to 60 degrees.

* * * * *